(12) United States Patent
Blatt et al.

(10) Patent No.: US 7,887,750 B2
(45) Date of Patent: Feb. 15, 2011

(54) ANALYTICAL SYSTEMS, DEVICES, AND CARTRIDGES THEREFOR

(75) Inventors: Joel M. Blatt, Mountain View, CA (US); Carole R. Stivers, Palo Alto, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 10/840,344

(22) Filed: May 5, 2004

(65) Prior Publication Data
US 2005/0249633 A1 Nov. 10, 2005

(51) Int. Cl.
*G01N 33/49* (2006.01)

(52) U.S. Cl. .................. 422/58; 422/68.1; 436/164; 436/169

(58) Field of Classification Search .......... 422/56–61, 422/68.1, 82.05; 436/56, 164, 166, 169
See application file for complete search history.

(56) References Cited

U.S. PATENT DOCUMENTS

| | | | |
|---|---|---|---|
| 4,784,145 A | 11/1988 | Ahsbahs et al. | |
| 4,790,979 A | 12/1988 | Terminiello et al. | |
| 4,943,522 A | 7/1990 | Eisinger et al. | |
| 5,100,626 A | 3/1992 | Levin | |
| 5,223,219 A | 6/1993 | Subramanian et al. | |
| 5,311,604 A | 5/1994 | Rogner et al. | |
| 5,837,551 A | 11/1998 | Ekins | |
| 5,952,173 A | 9/1999 | Hansmann et al. | |
| 5,962,215 A | 10/1999 | Douglas et al. | |
| 6,082,185 A | 7/2000 | Saaski | |
| 6,106,780 A * | 8/2000 | Douglas et al. ............ 422/58 |
| 6,228,574 B1 | 5/2001 | Rotman | |
| 6,391,261 B1 | 5/2002 | Liang et al. | |

(Continued)

FOREIGN PATENT DOCUMENTS

EP 0 397 424 A2 11/1990

(Continued)

OTHER PUBLICATIONS

Boldt, M. et al. (May 1980). "A Sensitive Dual Wavelength Microspectrophotometer for the Measurement of Tissue Fluorescence and Reflectance," *Pflügers Arch.* 385:167-173.

(Continued)

*Primary Examiner*—Lyle A Alexander
(74) *Attorney, Agent, or Firm*—Lerner, David, Littenberg, Krumholz & Mentlik, LLP

(57) ABSTRACT

Described here are systems, devices, cartridges, methods, and kits for detecting or quantifying at least two different analytes using at least two different techniques, in a single sample. The cartridges typically comprise at least two test sites and the location of at least one test site is not dependent on a corresponding measurement device. The systems generally comprise a device, memory, and a processing module. The device comprises a light source, an array detector, and a port configured to accept at least a portion of a cartridge. The processing module is configured to perform an image analysis of the cartridge. The methods comprise the steps of acquiring calibration information, acquiring an image of the cartridge, performing an image analysis, and cycling through specific detection or quantification techniques corresponding to the techniques required by the test sites. Computer readable media are also described.

22 Claims, 16 Drawing Sheets

U.S. PATENT DOCUMENTS

| | | |
|---|---|---|
| 6,403,947 B1 | 6/2002 | Hoyt et al. |
| 6,417,506 B1 | 7/2002 | Pinkel et al. |
| 6,605,813 B1 | 8/2003 | Kovalsky et al. |
| 6,608,117 B1 | 8/2003 | Gvozdic |
| 6,613,539 B1 | 9/2003 | Becker et al. |
| 6,626,051 B2 | 9/2003 | Zwick et al. |
| 6,645,142 B2 | 11/2003 | Braig et al. |
| 6,665,072 B2 | 12/2003 | Hoyt |
| 6,673,533 B1 | 1/2004 | Wohlstadter et al. |
| 6,690,466 B2 | 2/2004 | Miller et al. |
| 6,720,149 B1 | 4/2004 | Rava et al. |
| 6,824,663 B1 | 11/2004 | Boone |
| 6,846,645 B2 | 1/2005 | Xue et al. |
| 6,859,280 B2 | 2/2005 | Kempen |
| 7,374,719 B2 * | 5/2008 | Anaokar et al. ............... 422/58 |
| 2003/0068666 A1 | 4/2003 | Zweig |
| 2004/0037738 A1 * | 2/2004 | Maus et al. .................. 422/56 |
| 2004/0053322 A1 | 3/2004 | McDevitt et al. |

FOREIGN PATENT DOCUMENTS

| | | |
|---|---|---|
| EP | 0 397 424 A3 | 11/1990 |
| EP | 0397 424 | 11/1990 |
| WO | WO 99/46045 | 9/1999 |
| WO | WO-99/46045 A1 | 9/1999 |
| WO | WO 01/17797 | 3/2001 |
| WO | WO-01/17797 A1 | 3/2001 |
| WO | WO 01/68921 | 9/2001 |
| WO | WO-01/68921 A2 | 9/2001 |
| WO | WO-01/68921 A3 | 9/2001 |
| WO | WO 2005/116632 | 12/2005 |

OTHER PUBLICATIONS

Lehr, H.A. et al. (Jan. 1999). "Complete Chromogen Separation and Analysis in Double Immunohistochemical Stains Using Photoshop-Based Image Analysis," *J. Histochem. Cytochem.* 47(1):119-125.

Neeley, W.E. (Nov. 1988). "A Reflectance Photometer with a Square Photodiode Array Detector for Use on Multilayer Dry-Film Slides," *Clin. Chem.* 34(11):2367-2370.

Starp, H. et al. (Sep.-Oct. 2000). "Novel Teststrip with Increased Accuracy," *Fresenius J. Anal. Chem.* 368:203-207.

Neeley, W., "A Reflectance Photometer with a Square Photodiode Array Detector for Use on Multilayer Dry-Film Slides," *Clinical Chem.*, 34(11):2367-70 (1988).

Neeley, W. et al., "Reflectance Digital Matrix Photometry," *Clinical Chem.*, 29(6):1038-41 (1983).

* cited by examiner

A

B

C

D

E

F

ANALYTICAL SYSTEMS, DEVICES, AND CARTRIDGES THEREFOR

FIELD

In general, this invention is in the field of multiple analyte detection and quantification, and more specifically, multiple analyte detection and/or quantification using more than one measurement technique, a single sample, and a single device.

BACKGROUND

Currently, it is common practice to detect or quantify distinct analytes using distinct detection or quantification techniques. For example, enzyme assays, immunoassays, chemical calorimetric assays, fluorescence labeling and measurement, chemiluminescent labeling and measurement, and electrochemiluminescent labeling and measurement, are a few exemplary well-known analytical techniques that may be used to detect the presence of various analytes. Many of these techniques are performed on a test strip or cartridge.

The test strips typically have specific zones or sites for testing located at various positions about the strip. Some of these strips contain an array of test sites for the multiple testing of a single analyte, or for the simultaneous testing of multiple analytes. Depending on the specific detection or quantification technique used, the test strips may or may not be used in combination with a separate measurement device. For example, where quantitative optical detection is required, an additional measurement device is also required to read the results of the test strip or cartridge. This is unlike the case with qualitative visual assays, for example, like those used in most over-the-counter pregnancy tests, where an observable color change on the test strip itself indicates the results of the test. Perhaps the best known example of a test strip used in combination with a separate device is a glucose test strip used in combination with a glucose meter.

However, independent of whether additional measurement devices are employed with the test strips, different detection and quantification techniques are not typically combined together. This is partly because each technique has a unique sensitivity, robustness, and tolerance. In addition, each technique typically has unique physical and chemical requirements. Further, it is often the case that the physical location of the test site read zones must be fixed or predetermined in order to enable a corresponding measurement device to read the test results. This is because the optical components within the measurement device are at a fixed location and the read zone must, therefore, be in a fixed location corresponding with the optical components so that a reading may be obtained (e.g., typical in most optically read glucose test strips).

In addition, the test sample dilution factor and detection system required to obtain the optimal testing conditions for one analyte are often incompatible with the dilution factor and detection system required for a second analyte. Thus, in order to test for both analytes, the user must either take multiple samples from the patient for use with different test strips, or draw one large sample for division into multiple samples so that the multiple samples may be used as different samples for different test strips. Requiring that multiple samples, or one large sample, be withdrawn is not only inconvenient for the patient, but can be painful as well, for example, when the sample is blood and it is withdrawn via venipuncture or multiple finger lances.

Therefore, running multiple tests on a single cartridge when multiple detection or quantification techniques are required or are desirable has heretofore been limited. Indeed, when the use of different techniques is required or desirable, the user most often employs multiple instruments, sometimes from multiple vendors, in order to obtain the test results. In the case where the user is a physician or laboratory technician, these devices can clutter and reduce the availability of highly valued bench space.

In addition, commercially available analytical devices are limited in that they either measure a single analyte or, if they can measure multiple analytes, require a large sample size. For example, the DCA 2000 system (Bayer Corporation, Diagnostics Division, Tarrytown, N.Y.) can measure hemoglobin A1c ("HbA1c") using a very small sample (1 μL) of blood, but can only detect a single analyte on a single cartridge using a small volume. It is a one analyte per cartridge test. When the DCA 2000 is configured to detect more than one analyte on a single cartridge, the sample volume required is much larger. For example, a test to detect microalbumin and creatinine requires a 40-μL urine sample. Similarly, the Piccolo Point of Care Chemistry and Electrolyte System (Abaxis, Inc., Union City, Calif.) can run a panel of up to about 12 tests, but it requires 100 μL of a blood, plasma or serum sample.

Generally, commercially available analytical devices are also limited in that they are not capable of performing software updates (e.g., assay improvements or menu expansions) in a manner transparent to the user. Further, although some devices designed for point-of-care medical use perform automatic Quality Control ("QC") checks, many ask the user to run control samples manually to assure accurate performance. The user is also asked to upload software or data for new assays, etc., manually. These operations require the user to have a more intimate knowledge of QC testing requirements and instrument maintenance than many potential users are willing or are able to acquire. In addition, devices without automatic update capabilities inevitably wind up obsolete as new tests, algorithms, and procedures are developed.

Accordingly, it would be desirable to have systems, devices, and cartridges capable of performing multiple tests on a single sample, using more than one detection or quantification technique. In addition, it would be desirable to provide cartridges and devices capable of performing these features using a small sample volume. It would also be desirable to have a device that provides automatic QC checks, updates, and data storage.

All patents, publications, journal articles, and other references cited herein are incorporated by reference in their entirety, as if each had been incorporated by reference individually.

SUMMARY

Described herein are systems, devices, cartridges, and kits for detecting and/or quantifying at least two different analytes using at least two different techniques, in a single sample. Methods for detecting two different analytes using at least two different techniques are also described. In general, the cartridges described here comprise at least two test sites for the detection or quantification of at least two different analytes and are configured to use at least two different techniques for the detection or quantification of the at least two different analytes. The precise location of at least one test site read zone is not dependent on a corresponding measurement device.

The cartridges may comprise a bottom layer, wherein at least a portion of the bottom layer is non-porous, a sample distribution layer, and at least two test sites having at least two test site read zones. The test sites are typically embedded in, or are adjacent to, the sample distribution layer and are configured to detect at least two analytes using two different techniques. As noted above, the location of at least one test site read zone is not dependent on a corresponding measurement device.

In some variations, the sample distribution layer comprises a porous material; in other variations, the sample distribution layer comprises an open channel capillary layer. The cartridge can also include a red blood cell separating layer, alone, or in combination with a retaining layer. The retaining layer is configured to adhere together the bottom layer, the sample distribution layer, the test sites, and any additional optional layers.

In some variations, the cartridge comprises at least three test site read zones. In other variations, the cartridge comprises at least, four, five, or six test site read zones. At least one test site may be configured to detect or quantify an analyte that is treatment, disease, disorder, or ailment specific. Similarly, at least one test site may be configured to detect or quantify an analyte that is a substance of abuse, a medicament or a by-product thereof, an environmental toxin or contaminant, or a biological or chemical warfare agent. The test sites may be of the same height, or may be of different heights. Similarly, some test sites may be of the same height while other test sites on the same cartridge may be of a different height. As should be evident, a mixture of heights on a single test cartridge is possible.

The cartridge can further comprise a unique identifier tag, such as a bar code, a mechanical pattern, a microchip, or a printed pattern. The cartridge may also be packaged in a sealed, but openable moisture resistant package. In some variations, the cartridge is configured to accept a sample volume of about 20 µL or less, and in some variations the sample is a bodily fluid, such as whole blood, plasma, serum, sweat, saliva, tears, interstitial fluid, spinal fluid, ocular fluid, pus, milk, semen, amniotic fluid, vaginal secretions, mucous secretions, and urine.

Systems for detecting or quantifying at least two different analytes are also provided. In general, the systems comprise a device, memory, and a processing module. The device comprises a port configured to accept at least a portion of a cartridge, the portion having at least two test site read zones, a light source, and an array detector. The device may also have electrical contacts for communication with electrochemical tests on the cartridge. The processing module is configured to receive signals from the array detector and to perform an image analysis of the cartridge to identify the location of the test site read zones and the optimal portions of the image for accurate and precise determination. The system enables the detection or quantification of the at least two analytes using at least two different detection or quantification techniques. These detection or quantification techniques can be independently selected from the group consisting of enzyme assays, specific binding assays, immunoassays, nucleic acid hybridization assays, fluorescence labeling, chemiluminescent labeling, electrochemiluminescent labeling, fluorescence measurement, chemiluminescent measurement, electrochemiluminescent measurement, reflectance measurement, transmittance measurement, absorbance measurement, turbidity measurement, electrochemistry, and combinations thereof. The preferred location of these detection techniques is not fixed in that their locations may be independently selected to be optimal for the functioning of each cartridge test combination.

The processing module may also be configured to determine an error condition, for example conditions such as an expired cartridge, an inadequate sample volume, an impossible analyte value, a reagent malfunction, a mechanical malfunction, an electronic malfunction, and mixtures thereof. Similarly, the processing module may be automatically upgradeable. In addition, the system may be configured to read a unique identifier tag on the cartridge, and the system may be self-calibrating. The system may also comprise a server connection line, non-volatile memory, a computer, or mixtures thereof. Systems, devices, and methods for automatically obtaining software upgrades, new test software algorithms, specific lot calibration information, specific lot expiration information, and related software and data are also provided.

Kits for detecting or quantifying at least two different analytes are also described here. In general, the kits comprise cartridges, with or without optional instructions. In some variations, the kits comprise the system described just above, and a cartridge. The cartridges of the kits may be configured so that at least a portion of the cartridge is configured to protrude from the port of the device. This protruding portion may comprise a red blood cell separator, a unique identifier tag, or mixtures thereof. The cartridge may also be disposable.

Devices for detecting or quantifying at least two different analytes are also provided here, and typically comprise a port configured to accept at least a portion of a cartridge, the portion having at least one test site read zone, a light source, an array detector, memory, and a processing module. The processing module is configured to receive signals from the array detector and to perform an image analysis of the cartridge to identify the location of the test site read zones. The device enables the detection or quantification of the at least two analytes using at least two different detection or quantification techniques.

The light source may comprise at least one light emitting diode ("LED"), an incandescent lamp or other radiant energy source emitting a broad range of wavelengths, with or without a filter wheel, or combinations thereof. The array detector typically comprises charge coupled device ("CCD") or complementary metal-oxide semiconductor ("CMOS") technology. The processing module may be configured to determine an error condition, such as those mentioned above. The device may also be configured to read a unique identifier tag on the cartridge. The device may also comprise polarization optics, a back-up power source, non-volatile memory, and combinations thereof. In some variations, the device occupies no more than about 1 cubic foot of volume.

A computer readable medium containing code for performing an image analysis of a cartridge is also described here. Generally speaking, the cartridge has at least two test site read zones, for the detection or quantification of at least two different analytes and is configured to use at least two different techniques for the detection or quantification of the at least two different analytes. The image analysis identifies the location of at least one test site read zone. In some variations the computer readable medium is firmware, in other variations, the computer readable medium is software.

Also described here are methods for detecting the presence or absence of, or for quantifying, at least two different analytes on a single cartridge using at least two different detection or quantification techniques. In general, the methods typically comprise the steps of acquiring calibration information for a cartridge having at least two test site read zones, acquiring an image of the cartridge using an array detector, performing an image analysis of the cartridge to identify the location of at least one test site read zone, and cycling through specific detection or quantification techniques corresponding to the detection or quantification techniques required by the test sites, wherein at least two different techniques are used.

DETAILED DESCRIPTION

Figure 1A:
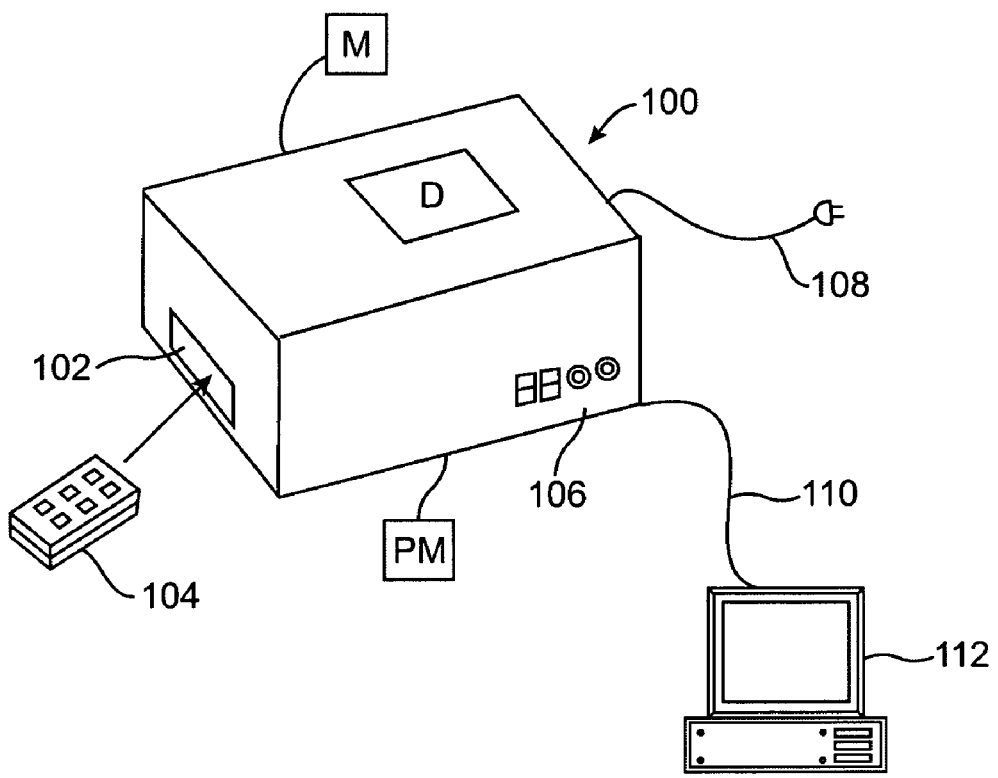
FIGS. 1A and 1B provide illustrative schematics of suitable systems and devices as described herein.

In general, the cartridges, systems, and devices described herein are capable of detecting or quantifying at least two different analytes using at least two different techniques, and are capable of using these different techniques to test a single sample. Thus, tests requiring different detection techniques due to different sensitivity requirements or chemistries, for example, can be combined in the same test cartridge and can be run using a single sample. Having the capability to measure multiple analytes using different techniques may provide greater flexibility in the types of tests that can be run, and greater flexibility in the number and location of individual test sites on the cartridge.

It should be understood that when the phrase detecting or quantifying is used throughout the specification, it is meant to include detection (e.g., detecting the presence or absence of an analyte) or quantification (e.g., quantifying the amount of analyte present in a given sample), alone, or in combination. Detection and quantification are not mutually exclusive for the purposes described herein. Examples of detection and quantification techniques suitable for use with the devices and cartridges described herein include enzyme assays, specific binding assays, immunoassays, fluorescence labeling and measurement, chemiluminescent labeling and measurement, electrochemiluminescent labeling and measurement, reflectance measurement, transmittance measurement, absorbance measurement, turbidity measurement, electrochemistry, and combinations thereof. As should be apparent, also included within this description is the use of two different types of the same technique (e.g., two different types of electrochemistry techniques) therefore, making the two techniques "different." For example, competitive and sandwich immunoassays are different techniques, as are heterogeneous and homogenous immunoassays. Similarly, an immunoassay employing reflectance measurement is a different technique from the same type of immunoassay employing fluorescence measurement. In this manner, two or more different concentration ranges of an analyte may be performed and fall within the scope of this invention if a different technique is employed for measurement of each concentration range.

I. General Uses

The systems, devices, and cartridges described herein may be used for any number of purposes. For example, they may be used for comprehensive diagnostic testing for use at a physician's office, clinic, pharmacy, hospital bedside, emergency room, mobile medical facility, military facility, or the like. That is, a cartridge may be configured to run multiple tests to aid in the diagnosis of a particular disease, disorder, or ailment. For example, someone suffering from a sore throat may be tested for strep throat, mononucleosis, pharyngitis, tonsillitis, and the like, using a single cartridge and a single sample. Similarly, someone suspected of suffering from a sexually transmitted disease may be tested for chlamydia, genital herpes, AIDS, gonorrhea, syphilis, and the like, using a single cartridge and a single sample. This is so even though different analytes may need to be detected using different technologies in order to confirm the presence or absence of a particular disease.

The cartridges and devices described herein may also be configured to run multiple tests in order to ascertain levels of particular analytes of interest. This may be useful, for example, in order to detect ineffectively low, as well as potentially hazardous high, blood analyte concentrations. This type of configuration may also be useful to detect the presence of a particular disease (e.g., diabetes, hypothyroidism, etc), monitoring a disease, stratification of a disease, and/or assessing risk for a given disease or condition. For example, typically more than one analyte (or elevated concentrations of various analytes) are associated with a given disease, and the detection of these analytes (or the detection of their elevated concentrations) can help determine from which disease a person may be suffering.

This type of configuration may also be used to monitor patient compliance with various treatment regimes. For example, blood may be taken as a sample, and the concentration of various medications in the blood may be quantified. Monitoring patient compliance may be particularly useful in the case of psychotic patients, where it may be difficult to otherwise determine compliance (e.g., by simply asking the patient). Thus, by way of example, a psychiatrist may obtain critical information about a mood stabilizer concentration in the bloodstream of a patient, as well as the safety of that blood level as it may affect the health of various organs. That is, potentially adverse side-effects involving injury to the liver, kidneys, or other internal organs for which there are corresponding and specific detectable substances in the bloodstream, may be monitored in this way. For example, in the case of treating bipolar disorder, valproic acid may be administered. A test may be configured to monitor the valproic acid concentration (to make sure the treatment is effective), while at the same time configured to monitor various enzymes of interest to ensure that liver damage does not occur. A typical combination of tests on a single cartridge for this type of analysis, for example, might include test sites for valproic acid and liver enzymes such as alanine aminotrasferase ("ALT," "SGPT"), aspartate aminotransferase ("AST," "SGOT"), and lactate dehydrogenase ("LDH").

The cartridges may also be configured to run tests for various substances of abuse. These substances may include street drugs such as heroin, cocaine, crystal meth, ecstasy, lysergic acid diethylamide ("LSD"), and the like, which may be particularly useful for the police force. Similarly, these tests may also be useful for physicians, by helping them rapidly detect a particular drug overdose when a patient arrives at the hospital unconscious, for example. The substances of abuse may also include various steroids, which may be particularly useful for testing athletes prior to competition.

In addition to medical applications, the systems, devices, cartridges, kits, and methods described here may also find utility in areas such as environmental and food testing. For example, the cartridges may be configured to detect various environmental toxins or contaminants (e.g., mercury, lead, heavy metals, etc.) in order to determine compliance with certain environmentally set standards. Similarly, the cartridges may be configured to detect or quantify environmental toxins and contaminants in a patient sample. Foods may also be tested for various contaminants using the cartridges, systems, and devices described here. As will be discussed in more detail below, in instances where food is used as a sample, it is likely that the food will need to be homogenized in a suitable medium to provide a fluid form.

The systems, devices, and cartridges may also be configured to detect or quantify various biological and chemical warfare agents. This may be useful during times of war, for example, for use at various military facilities.

Below is a list of exemplary analytes suitable for detection using the systems, devices, cartridges, kits and methods described herein, as well as their clinical utilities, and biological or therapeutic concentration ranges (taken from Norbert W. Tietz, "Textbook of Clinical Chemistry." W.B. Saunders Company, Philadelphia, Pa., 1986). It should be noted, that when reference is had to the detection of at least two different analytes, it is meant to include the case wherein the at least two different analytes are structurally and chemically the same, however, having different concentration ranges. As should be evident, any type of analyte may be tested using the systems, devices and cartridges herein described. Accordingly as used herein, when reference is had to the term "analyte," it should be understood that such term is meant to include any chemical entity, such as a protein, DNA (single stranded or fragments thereof), small molecule, or the like, which may be quantitatively or qualitatively detected. The following table is meant to be illustrative only, and in no fashion limiting.

TABLE 1

Exemplary analytes, their clinical utilities, and their biological or therapeutic concentration ranges.

| Analyte | Utility | Typical Concentration Range (Serum or Plasma) |
|---|---|---|
| Alanine Aminotransferase (ALT, SGPT) | Liver | 5-28 U/L |
| Albumin (plasma) | Liver | 3.4-5.2 g/dL |
| Albumin (urine) | Kidney | <80 mg/day |
| Amakacin | Antibiotic for Severe Infection (Hospital) | 1-40 µg/mL (1.7-68 µmol/L) |
| Amitriptyline | Depression | Therap: 125-250 ng/mL (433-903 nmol/L) Toxic: >500 ng/mL (>1805 nmol/L) |
| Amylase | Pancreas | 20-160 U/L |
| Aspartate Aminotransferase (AST, SGOT) | Liver | 8-75 U/L |
| Bilirubin | Liver | <2-<16 mg/dL (34.2-274 µmol/L) |
| Brain Natriuretic Peptide (BNP) | Congestive Heart Disease | 2-22 pg/mL (up to ~200 pg/mL with heart disease or renal failure) |
| Calcitonin (hCT) | Bone formation | 30-670 pg/mL |
| Cancer chemotherapeutic agents | Cancer | Various |
| Carbamazepine | Epilepsy, Bipolar Disorder | Therap: 8-12 µg/mL (34-51 µmol/L) Toxic: >15 µg/mL (>63 µmol/L)) |
| Cardiac Troponin I (cTnI) | Acute Myocardial Infarction | ≦0.3-120 ng/mL |
| Cholesterol (HDL) | Diabetes & Heart Disease | 5-85 mg/dL (0.13-2.2 mmol/L) |

TABLE 1-continued

Exemplary analytes, their clinical utilities, and their biological or therapeutic concentration ranges.

| Analyte | Utility | Typical Concentration Range (Serum or Plasma) |
|---|---|---|
| Cholesterol (LDL) | Diabetes & Heart Disease | 10-235 mg/dL (0.26-6.09 mmol/L) |
| Cholesterol (total) | Diabetes & Heart Disease | 45-310 or more mg/dL (1.17-8.03 or more mmol/L) |
| Chorionic Gonadotropin (hCG) | Pregnancy | <3-140,000 mIU/mL |
| Cortisol | Endocrinology | 5-23 µg/dL (83-635 nmol/L) |
| C-Reactive Protein (CRP) | Infection, Heart Disease & Atherosclerosis | 1-825 µg/dL |
| Creatine | Kidney; Muscle | 0.17-0.93 mg/dL (13-71 µmol/L) |
| Creatine Kinase (activity) | Acute Myocardial Infarction (AMI) | 10-200 U/L |
| Creatine Kinase Isoenzyme MB (CKMB) | Acute Myocardial Infarction (AMI) | ≦7 ng/mL; 39-185 ng/mL peak during AMI |
| Creatinine (blood) | Kidney | 0.2-1.2 mg/dL (18-106 µmol/L) |
| Creatinine (urine) | Kidney; Normalization of Analyte Concentration | 8-26 (mg/d)/kg (71-230 µmol·d$^{-1}$·kg$^{-1}$) |
| Digoxin | Cardiac Arrythmias | Therap: 0.8-2.0 ng/mL (1.0-2.6 nmol/L) Toxic: >2.5 ng/mL (>3.2 nmol/L) |
| Estradiol | Endocrinology | 0-500 pg/mL (0-1835 pmol/L) |
| Estriol (Free & Total) | Endocrinology | 1.0-350 µg/L (12.1-1215 nmol/L) |
| Estrogens, Total | Endocrinology | <30-31,000 pg/mL (ng/L) |
| $\alpha_1$-Fetoprotein (AFP) | Fetal Development | Plasma: ≦1-16.5 µg/dL (≦10-165 µg/L) Amniotic Fluid: 0.02-5.0 mg/dL (0.2-50 mg/L) |
| Follicle Stimulating Hormone (hFSH) | Fertility | 1-250 mIU/mL (IU/L)) |
| Gentamycin | Antibiotic for Severe Infection (Hospital) | 1-10 µg/mL (2.1-20.9 µmol/L) |
| Glucagon | Endocrinology | 11-117 pg/mL (ng/L) |
| Glucose | Diabetes | 20-400 mg/dL (1.11-22.2 mmol/L) |
| Haptoglobin | Detection and Monitoring of Acute Phase Reactions and Hemolytic States | 26-267 mg/dL (260-2670 mg/L) |
| HbA1c | Diabetes | 2-20% |
| Hemoglobin | Anemia | WB: 9-22.5 g/dL (1.4-3.49 mmol/L) Plasma: 1-4 mg/dL (0.16-0.62 µmol/L) |
| Homocysteine | Heart Disease Risk | Normal: 5-15 µmol/L Abnormal: 16-100+ µmol/L |
| Kanamycin | Antibiotic for Severe Infection (Hospital) | 1-40 µg/mL (2-82 µmol/L) |
| Lactate Dehydrogenase (LDH; lactate → pyruvate) | Liver | 55-1500 U/L (30° C.) |
| Lithium | Bipolar Disorder | Therap: 0.6-1.2 mEq/L (mmol/L) Toxic: >2 µg/mL mEq/L (mmol/L) |
| Luteinizing Hormone (hLH) | Fertility | 3-200 mIU/mL (IU/L) |
| Myoglobin | MI | 21-66 µg/L (5-1000 µg/L assay range) |
| Nortriptyline | Depression | Therap: 50-150 ng/mL (190-570 nmol/L) Toxic: >500 ng/mL (>1900 nmol/L) |
| Paraquat | Toxic Chemical | 0.1-64 µg/mL (0.39-249 µmol/L) |
| Parathyroid Hormone (hPTH) | Calcium Metabolism & Bone | N-term: 230-630 pg/mL (ng/L) C-term: 430-1860 pg/mL (ng/L) Immuno Nuclear Mid Molecule: 0.29-0.85 ng/mL (29-85 pmol/L) |
| Phenobarbital | Epilepsy | Therap: 15-40 µg/mL (65-170 µmol/L) Toxic: >35 µg/mL (>151 µmol/L) |
| Phenytoin (diphenylhydantoin) | Epilepsy | Therap: 10-20 µg/mL (40-79 µmol/L) Toxic: >20 µg/mL (>79 µmol/L) |
| Phosphatase, Acid | Prostate | <3.0 ng/mL (µg/L) 0.11-0.60 U/L |
| Phosphatase, Alkaline (ALK-P) | Bone and Liver Diseases/Cancer | 20-165 U/L |
| Potassium | Electrolyte Status | 3-12 mEq/L (mmol/L) |
| Progesterone | Fertility | 0.11-30 ng/mL (0.35-95.4 nmol/L) |
| Prostate Specific Antigen (PSA) | Prostate Cancer & Prostate Hyperplasia | Normal: 0-4 ng/mL (0-0.12 nmol/L) Cancer: 50+ ng/mL (+1.52 nmol/L) Ultrasensitive (Recurrence): ≧0.01 ng/mL (0.3 pmol/L) |
| Protein, Total | Nutritional Status; Disease Diagnosis | 3.6-8.0 g/dL (36-80 g/L) |
| Renin | Blood Pressure | 0.1-13.2 (ng/h)/mL (µg·h$^{-1}$·L$^{-1}$) |
| Sodium | Electrolyte Status | 116-166 mEq/L (mmol/L) |
| Somatotropin (hGH) | Endocrinology | <1-50 ng/mL (µg/L) |
| Testosterone | Endocrinology | Free: 0.03-10.2 ng/dL (1.05-354 pmol/L) Total: 5-707 ng/dL (0.17-24.6 nmol/L) |
| Theophylline | Asthma | Therap: 6-20 µg/mL (44-111 µmol/L) Toxic: >20 µg/mL (>110 µmol/L) |
| Thyroid Microsomal Antibodies | Thyroid | ND or <1:10 dilution (IFA) |
| Thyroid Stimulating Hormone (hTSH) | Thyroid | 0.01-50 µIU/mL (mIU/L) Normal: 0.4-6.0 µIU/mL (mIU/L) |

TABLE 1-continued

Exemplary analytes, their clinical utilities, and their biological or therapeutic concentration ranges.

| Analyte | Utility | Typical Concentration Range (Serum or Plasma) |
|---|---|---|
| Thyroxine (T4) | Thyroid | Free: 0.8-2.4 ng/dL (10.3-31.0 pmol/L) |
|  |  | Total: 4.5-12 µg/dL (58-154 nmol/L) |
| Transferrin | Iron Metabolism | 130-400 mg/dL (1.3-4.0 g/L) |
| Triglycerides | Diabetes & Heart Disease | 10-288 mg/dL (0.11-3.25 mmol/L) |
| Triiodothyronine (T3) | Thyroid | Free: 120-660 pg/dL (1.85-10.16 pmol/L) |
|  |  | Total: 30-275 ng/dL (0.46-4.26 nmol/L) |
| Urea Nitrogen | Kidney | 3-40 mg/dL (1.1-14.3 mmol urea/L) |
| Uric Acid | Gout | 2.0-8.2 mg/dL (0.12-0.48 mmol/L) |
| Valproic Acid | Epilepsy, Bipolar Disorder | Therap: 50-100 µg/mL (347-693 µmol/L) |
|  |  | Toxic: >100 µg/mL (>693 µmol/L) |
| Vancomycin | Antibiotic for Severe Infection (Hospital) | Toxic: 80-100 µg/mL (mg/L) |
| Vitamins & Nutrients | Nutritional Status | Varies |
| Warfarin (coumadin) | Anticoagulant Therapy | 1-10 µg/mL (3-32 µmol/L) |

II. Systems

The systems described herein enable the detection or quantification of at least two different analytes using at least two different techniques. In general, the systems comprise a device, memory, and a processing module. The device comprises a port configured to accept at least a portion of a cartridge, a light source, and an array detector. The portion of the cartridge that enters the device has at least one of the two or more test site read zones for the detection or quantification of at least one of the two or more different analytes. However, as will be described in more detail below, any number of analytes may be detected using the systems, devices, and cartridges described herein, as is practicable or desirable.

Making reference now to the drawings, where like numerals indicate like elements throughout the views, FIG. 1A provides an illustrative example of how the system may be configured. Shown there is an external view of device (100), having a port (102), which is configured to accept at least a portion of a cartridge (104). The port may also include automatic insertion and ejection capabilities. Shown are various control knobs and switches (106), which may be useful to turn the device on, and control several of its features. A line to a power supply is provided (108) as well as a cable (110) to enable attachment to a processing module (PM) such as a computer or a personal computer ("PC") board (112) if desirable. Indeed, the device may be configured to include a PM, such as a PC board, a display (D) to display information (e.g., test results, maintenance updates, upgrade alerts, etc.), and a printer (not shown) to print out the test results, etc.

While the power supply line (108) is shown, it should be understood that the device may also be battery operated. In addition, the device may also have a back up power supply, for example, a battery (not shown), to help power the device in the case of a power outage. For this reason, it may also be desirable that the device has some non-volatile memory as well.

The device may also comprise a sliding, or otherwise openable (e.g., hinged) sample door (not shown). In this way, the sample door may be opened to enable access to the cartridge, once the cartridge is inserted into the device. The sample door, for example, may optimally be placed at a position corresponding to the location of the cartridge so that a sample may be placed on the cartridge with relative ease after the cartridge has been inserted into the device. Alternatively, the device may comprise a second access port that allows application of the sample after the cartridge is inserted into the device.

It should be understood that while device (100) is depicted here as having a rectangular form, the device may have any suitable or desirable geometry. The device may also be of any desirable size. In some variations, it may be desirable that the device has a size of about 2 cubic feet or less, or about 1 cubic foot or less, which would help minimize bench top clutter. Similarly, while the control knobs and switches (106) are depicted in FIG. 1A as located on the side of device (100), it should be understood that these knobs and switches may be located at any desirable or convenient place on the device. For example, they may be on the front of the device, on the back of the device, or combinations thereof. Some or all of the functions of these control knobs and switches may optionally be performed with a touch screen.

Figure 1B:
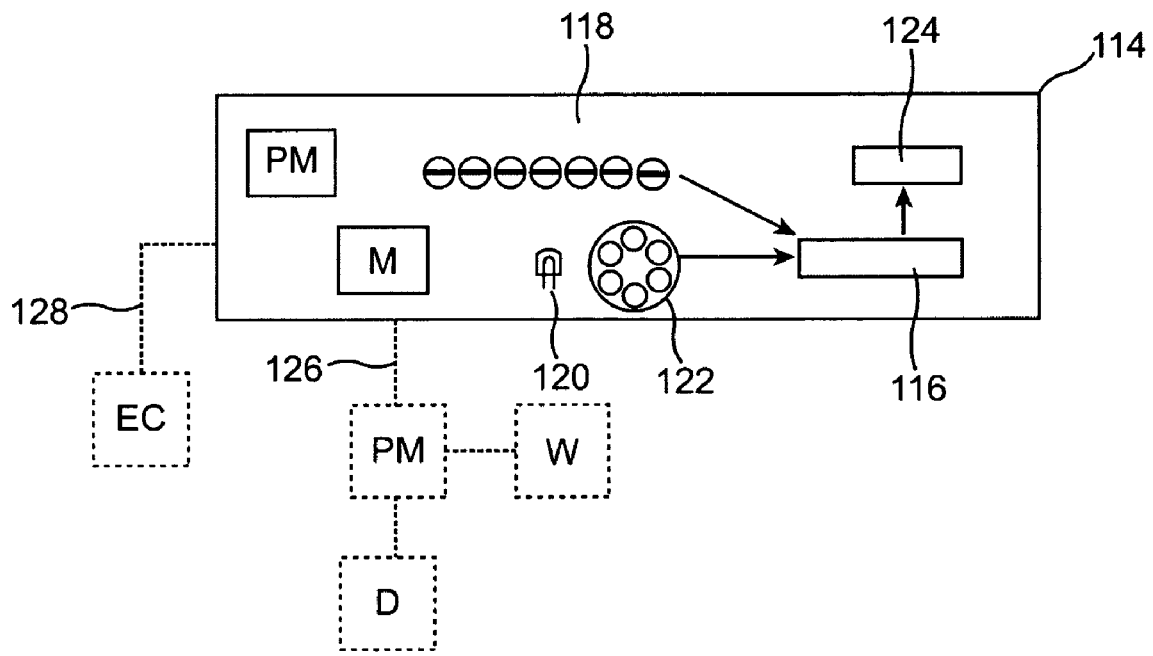

FIG. 1B provides an illustrative schematic of the inside of a device. As shown there, device (114) has cartridge (116) therein; Illustrative light sources are depicted by one or more LEDs (118) and an incandescent lamp (120). A filter wheel (122) may also be used. Multiple light sources may be housed within the device as shown in FIG. 1B, or only one light source may be used. The light source should be configured to direct light to the cartridge (116). The cartridge output is typically directed toward an array detector (124). The light sources may be configured to illuminate light onto the cartridge from below the cartridge, from the top of the cartridge, from the side of the cartridge, or combinations thereof. Accordingly, the array detector will typically be located at a convenient output location, depending on the direction of the light source input. The array detector (124) can comprise CCD technology, CMOS technology, or the like, as well known in the art.

Also shown in FIG. 1B is an optional cable (126) so that a PM (e.g., a PC board) may be connected to the device. A display (D) may be hooked up to the PM in order to monitor the results, and to display other information. Similarly, a wireless connection (W) or other internet connection capability (e.g., modem, cable, etc.) may be hooked up to the PM. Line (128) enables the device to be used with an additional electrochemistry measurement subsystem (EC) that may optionally be internal to the device. The EC may comprise conductors adapted for electrical connection with an electrochemical analyzer. As described above, an optional printer (not shown) may also be used with the device. Any or all of the foregoing elements (e.g., device, EC, PM, W, D, printer) may be optionally contained within a single housing.

As will be discussed in more detail below, the system may also be configured to read a unique identifier tag on the cartridge. In this way, the system may be able to identify the type, number, and approximate location of the test site read zones, as well as able to determine calibration, algorithm, and lot information therefor. Accordingly, the device may further comprise a scanning window to image the tag (similar to those used at grocery stores), a scanning or swiping slot (similar to those used with credit cards), or a non-contact electronic method of obtaining information from a microchip embedded in, or attached to, the cartridge. Similarly, the cartridge having a unique identifier tag thereon may be configured to be fully inserted into the device so that the tag can be read.

However, the system need not obtain the exact read zone information from the unique identifier tag. Indeed, the system comprises a processing module configured to receive signals from the array detector and to perform an image analysis, or scan of the cartridge in order to identify the type and location of the read zones. The processing module (PM) is shown in FIG. 1A as being external to the device, but it may also be within the device itself, as shown in FIG. 1B.

The processing module may be code or logic, implemented in hardware logic (e.g., an integrated circuit chip, Programmable Gate Array (PGA), Application Specific Integrated Circuit (ASIC), etc.) or in a computer readable medium such as, for example, magnetic storage medium (e.g. hard disk drives, floppy disks, tape), optical storage (e.g., CD-ROMs, optical disks, etc.), volatile and non-volatile memory devices (e.g., EEPROMs, ROMs, PROMs, RAMs, DRAMs, SRAMs, firmware, programmable logic, etc.). Code in the computer readable medium is accessed and executed by a processor.

Accordingly, also provided herein is a computer readable medium containing code for performing an image analysis of a cartridge comprising at least two test site read zones for the detection or quantification of at least two different analytes, and configured to use at least two different techniques for the detection or quantification of the at least two different analytes. The image analysis identifies the location of the at least two test site read zones. In some variations, the computer readable medium is firmware, and in other variations, it is software.

The image analysis may be performed in a manner described by Neeley in "Reflectance Digital Matrix Photometry." Clin. Chem. Vol. 29, No. 6, 1038-1041 (1983); "An Instrument for Digital Matrix Photometry." Clin. Chem. Vol. 27, No. 10 1665-1668 (1981); and "A Reflectance Photometer with a Square Photodiode Array Detector for Use on Multilayer Dry-Film Slides." Clin. Chem. Vol. 34, No. 11, 2367-2370 (1988), using algorithms developed for machine vision systems, or by similar algorithms for image algebra. In general, the processing module receives signals from the array detector that provide a general image of the cartridge. The areas to be measured are then subdivided, grid-like, into small subunits. Image analysis then proceeds by the identification of clusters of pixels that have similar intensity values, which are located within the outer edges of a larger cluster of pixels, and which are located approximately at the predetermined locations for the group of tests performed by the cartridge being used.

Therefore, in operation, the type and location of the particular test sites on the cartridge will first be identified. The system will typically then check to see if the test procedure, algorithm, and calibration values are stored in the system memory, in order to enable the tests to be run. As with the processing module (PM), the system memory (M) may be external to the device, as depicted in FIG. 1A, or it may be within the device itself, as depicted in FIG. 1B. The system memory may also be part of the processing module. If the system has previously encountered cartridges from the same manufacturing lot (and therefore having the same calibration parameter values, test procedures, and algorithms), the system will have this information stored in its memory. Therefore, the system may notify or signal to the operator that testing may proceed. The notification may occur, for example, as a word prompt on a display (e.g., LCD screen, etc.), by an audible signal, mixtures of prompts and signals, and the like.

If the algorithms and test procedures for the cartridge are present in the system memory, but the specific lot information (calibration parameters, expiration dating, etc.) is not, the system may automatically download these values from a remote source, such as a host server computer, via a server connection (e.g., a direct dial-up line, such as a land line, cell phone line, etc. or an internet connection, such as a cable or other wired line, wireless and satellite lines and the like). However, if the testing procedures, algorithms, and calibration parameters are not stored in the system memory (as might happen if the test has only recently been added to the menu of available tests), the system may download both the appropriate testing procedures and algorithms to run and interpret the test, as well as the specific lot information. If the cartridge employs electrochemical methods for detection, alone or in combination with optical methods, the active electrical contacts and their specific functions may be obtained and used in a similar manner. The processing module of the system may also contain executable code that enables the system to automatically transmit test results and sample ID information to a host server's confidential database for retrieval by authorized professionals. Any of the foregoing functions may also optionally be under the control of the user.

After the algorithms, test procedures, and lot information have been obtained, the system then utilizes the light source and the array detector to acquire an initial "dry"; image (or series of images) of the cartridge, as described above. That is, images of the cartridge surface are obtained under different conditions of illumination, for example, using selected wavelengths of radiation from one or more light sources, which are optionally combined with one or more filters in the detection light path. The system then stores the images in its memory for later use. The operator may now put a sample in the cartridge, as signaled by the system, as described above.

When the presence of a sample is detected (optically or by methods of employing an electrical change such as conductivity or capacitance), the processing module will direct the system to perform a variety of measurements specific for the test or combination of tests on the cartridge. This might result in three or more measurement modes being repeatedly activated in sequence. For example, a 605 nm LED might be turned on for reflectance measurements at two different read zones, and then a 500 nm LED might be turned on (and a filter inserted in the detection light path to block essentially all the light output from that LED) in order to perform fluorescence measurements at three different read zones. Images of the entire cartridge surface acquired under these two different conditions of illumination would be stored and compared to subsequent images taken under the same conditions.

When the change in pixel intensity in the general surface locations for the tests reaches a predetermined level of insignificance, or when the rate of change reaches a steady state, image acquisition is stopped and calculations are performed to determine the reflectance, fluorescence, etc., or the rate of change thereof, for each test region as appropriate for that test. These numerical values are then converted, using stored algorithms and calibration parameter values, into analyte concentrations that are reported via the display (D) on the device or on the PC, or by some other suitable method. These values may also be printed, communicated to a PC for storage in a patient database, or both. The operation of the system would be similar to the foregoing for tests requiring chemiluminescent or electrochemical detection, however, with these techniques, no light source would be needed. Electrochemical detection would not require any use of the optical capabilities of the device.

The processing module of the devices and systems described here may also be configured to detect particular error conditions. These error conditions may be, for example, the detection of an expired cartridge, an inadequate sample volume, an impossible analyte value, a reagent malfunction, a mechanical malfunction, and mixtures thereof. Should an error condition be detected, an appropriate signal can be displayed by the device. The display may further indicate whether device repair is required. This type of notification may help to facilitate the expeditious replacement of faulty parts. The processing module may also be configured to transmit the error condition to a host server via a server connection line. In this way, if repair is required, the owner of the host server may be able to intervene and help repair the system or device in a timely manner. In addition, the processing module can be configured to inactivate the system or device so that erroneous test results are not obtained or reported should the owner try to operate the system or device while it is malfunctioning.

In some variations, the processing module is automatically upgradeable. In these variations, the device may have a server line connection, enabling the connection to a remote source such as a host server. Here, the upgrading can occur automatically during the normal course of device operation without the need for involvement by the device operator. The server line connection may also provide for automatic communication with the host server on an as-needed basis. For example, automatic messages such as periodic maintenance reminders or notification of existing hardware or software upgrades may be sent to the system. In some variations, the system is also self-calibrating. That is, the system may perform routine calibrations using ratioing techniques, internal standards, and controls, and other techniques known in the art.

As should be evident from the system descriptions above, individual devices are also provided. In general, the devices comprise a port configured to accept at least a portion of a cartridge, the cartridge having at least two test site read zones and the portion having at least one test site read zone, a light source, an array detector, memory, and a processing module. The processing module is configured to receive signals from the array detector to perform an image analysis of the cartridge to identify the location of the read zones.

As described above, the light source may comprise one or more solid state devices (LEDs, laser diodes, or the like) or may comprise an incandescent lamp or other radiant energy source emitting a broad range of wavelengths (e.g., about 300 nm to about 1000 nm for a tungsten light source). A filter wheel may be optionally employed. The device may also comprise polarization technology to enable the performance of fluorescence polarization immunoassays. Similarly, the device may also be configured to detect temperature changes, and provide for temperature control.

III. Cartridges

In general, the cartridges comprise at least two test sites for the detection or quantification of at least two different analytes, and are configured to use at least two different techniques for the detection or quantification of the at least two different analytes. It should be understood that when reference is had to the phrase "test site," it is meant to describe an area, or areas, of a cartridge that are occupied by the reagents and zones necessary to perform a given test, as described herein. Obviously, some test sites will not require the use of any reagents. Similarly, the term "read zone" or "test site read zone" when referenced herein, is meant to describe the area, or areas, of the test site where the results of the test are obtained. Since the location of at least one of the read zones on the cartridge is identified by the system or device during testing, the exact location of at least one of the test sites and read zones need not be fixed. That is, the location of at least one of the test sites and read zones is not dependent upon a corresponding measurement device.

In general, the cartridges comprise a bottom layer, a sample distribution layer, and at least two different test site read zones. The bottom layer is typically non-porous (e.g., a plastic, glass, or the like) and may be transparent, when optical transmission measurement of analytes is desirable. The sample distribution layer allows the sample to flow to the various test sites. The test sample may be any suitable fluid. For example, the test sample may be a bodily fluid, such as whole blood, plasma, serum, sweat, saliva, tears, interstitial fluid, spinal fluid, ocular fluid, pus, milk, semen, amniotic fluid, vaginal secretions, mucous secretions, and urine. Similarly, the test sample may be water (suspected of being contaminated), or may be a food product. In cases where the sample is a food product, the food product will typically need to be ground up, or homogenized and mixed in an appropriate medium. Further manipulations may be required (such as extraction or purification) to prepare a sample suitable for testing. The test sites may be embedded in, or be adjacent to, the sample distribution layer and are configured to detect at least two analytes using two different techniques.

The cartridges may be configured to accept a small sample volume, for example, a 20 μL or 10 μL sample of blood. This provides the advantage of allowing multiple tests to be performed using a small sample volume. However, a sample may also be diluted to provide for a larger sample. For example a 10 μL volume of blood may be diluted ten fold to provide a sample volume of 100 μL. Therefore, multiple tests may be performed using a small sample of blood that has been extracted from a patient, and then subsequently diluted. In this way, patient pain may be minimized. Accordingly, the cartridges may be configured to accept any suitable sample volume.

Figure 2A:
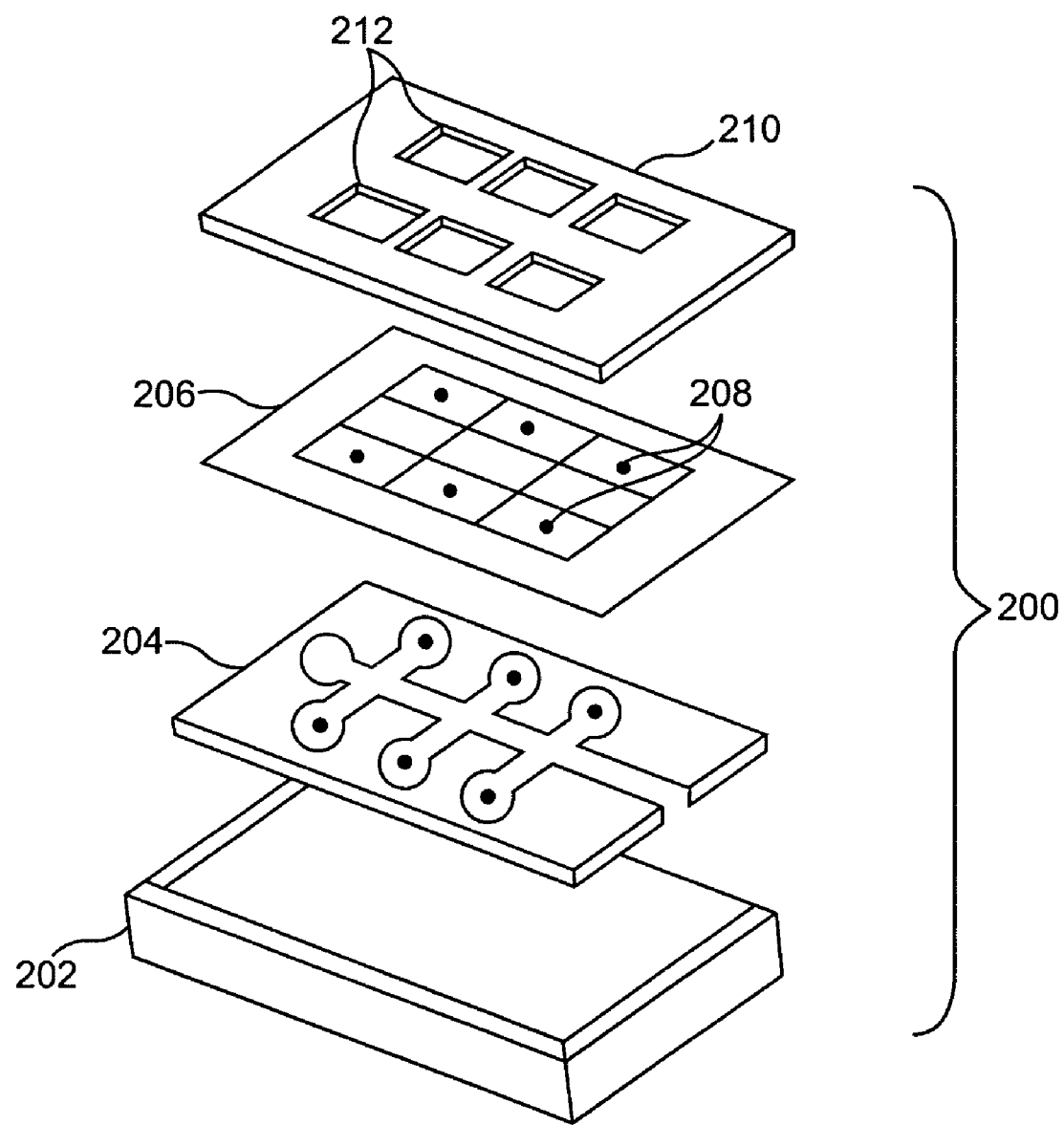
FIGS. 2A and 2B are exploded views depicting illustrative cartridge configurations.

An exploded view of one variation of a suitable cartridge is depicted in FIG. 2A. Shown there is cartridge (200) comprising a bottom layer (202), a sample distribution layer (204), a test site layer (206) having test sites (208), and a retaining layer (210). The retaining layer is shown as having transparent or open windows (212) for the optical detection of analytes from the corresponding test sites below. In this variation, bottom layer (202) and retaining layer (210) are typically constructed of a non-porous material, for example, plastic, glass, or the like, and sample distribution layer (204) is an open channeled capillary layer, punched out of plastic, for example. In this variation, the sample distribution layer (204) is sandwiched between the bottom layer (202) and the test site layer (206).

Figure 2B:
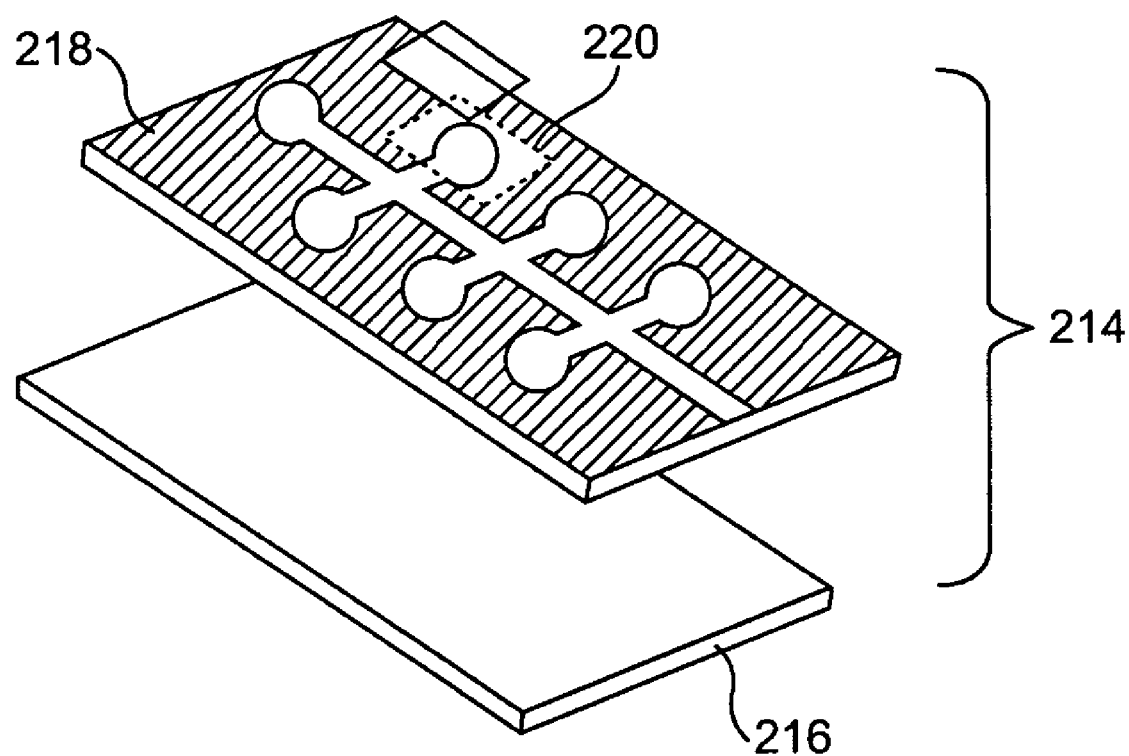

An exploded view of another suitable cartridge variation is depicted in FIG. 2B. Shown there is cartridge (214) comprising bottom layer (216), sample distribution layer (218), and test site (220). In this variation, sample distribution layer (218) may be constructed of a porous material or membrane having a hydrophobic surrounding, to limit or prevent fluid flow thereto. For example, the hydrophobic surrounding may be a wax, or the like, shown here by diagonal striping. Bottom layer (216) is typically made from a non-porous material.

An optional retaining layer (not shown) may also be employed to retain or hold the layers together. Such a layer may overlap entirely with the sample distribution layer, or may only overlap the sample distribution layer at its edges or corners. The retaining layer may also be a mesh, a nylon, or the like. In addition, the retaining layer may be occlusive or sealing in nature, in order to prevent evaporation therethrough. Of course, separate sealing layers, or portions thereof are also acceptable. As noted above, however, the retaining layer is optional, and the layers can be held together by any suitable fastening method. For example, the layers may be held together using mechanical clamping, snap-fitting, heat shrinking, gluing (using any suitable adhesive), and the like.

While not shown in FIG. 2A or 2B, the cartridge may also comprise a red blood cell separator layer, in order to remove the red blood cells before they reach the test sites. In this way, red blood cells that may interfere with certain optical measurements are removed. This layer may be placed immediately below the sample distribution layer, for example, and may be contemporaneous therewith, or only cover a portion thereof.

As shown in FIG. 2B, test site (220) is adjacent to the sample distribution layer and, as will be described in more detail below, is configured to detect a given analyte. Test site (220) is shown here as having two layers, but as will be evident from the test site description below, any number of layers as practicable or desirable may be used. In this way, the test sites may be of varying heights. That is, one test site may have only one layer, while another test site at a different location on the cartridge may have two or more layers. In addition, the test sites may be of varying widths and lengths.

Generally speaking, the sample distribution layer may be made using any number of techniques. For example, the sample distribution layer may be made using processes such as lasering, embossing, Lithographie Galvanoformung Abformung ("LIGA"), electroplating, electroforming, photolithography, reactive ion etching, ion beam milling, compression molding, casting, reaction injection molding, injection molding, micromachining, and the like.

In certain variations, it may be desirable to make the sample distribution layer using photolithography techniques. For example, polymers can be incorporated into a lateral flow or filtration membrane, using negative or positive photoresist-type materials. The photoresist materials could be impregnated into the membrane by screen-printing, spraying, dipping, reverse roller coating, gravure coating, or the like. The membrane would then be exposed to UV light, using a photolithography mask or reticle, so that certain areas are protected from exposure. The membrane would then be developed using an appropriate solvent to wash away material that had either not been polymerized (e.g., in the case of negative photoresist) or that have been converted to a soluble form (e.g., in the case of positive photoresist). Membrane development can be done in any number of ways. For example, the membrane can be developed using filtration on a flat bed, or by dipping the membrane into a suitable solvent.

Figure 2C:
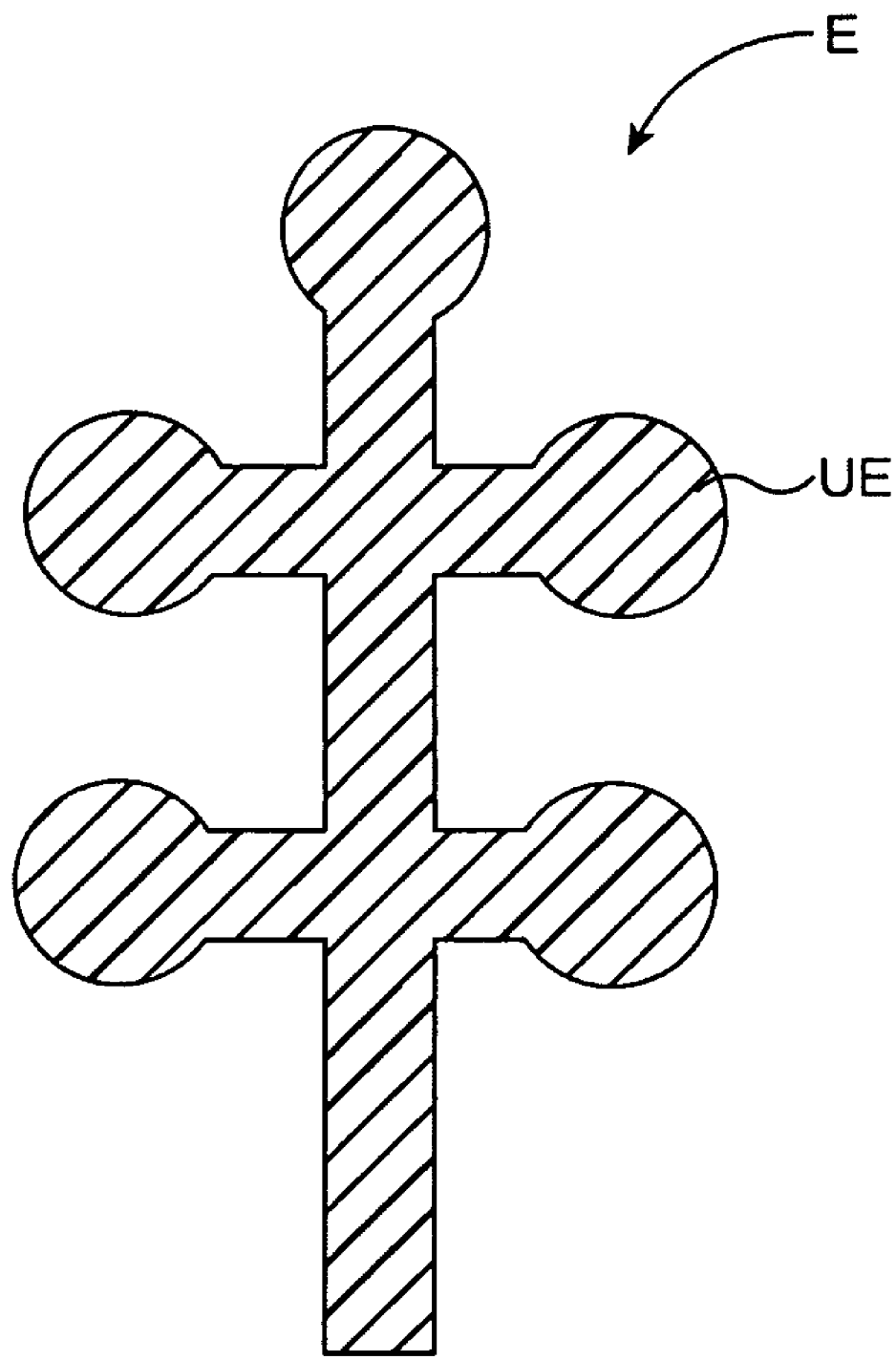
FIGS. 2C and 2D illustrate masks or reticles used with negative and positive photoresist techniques respectively.
Figure 2D:
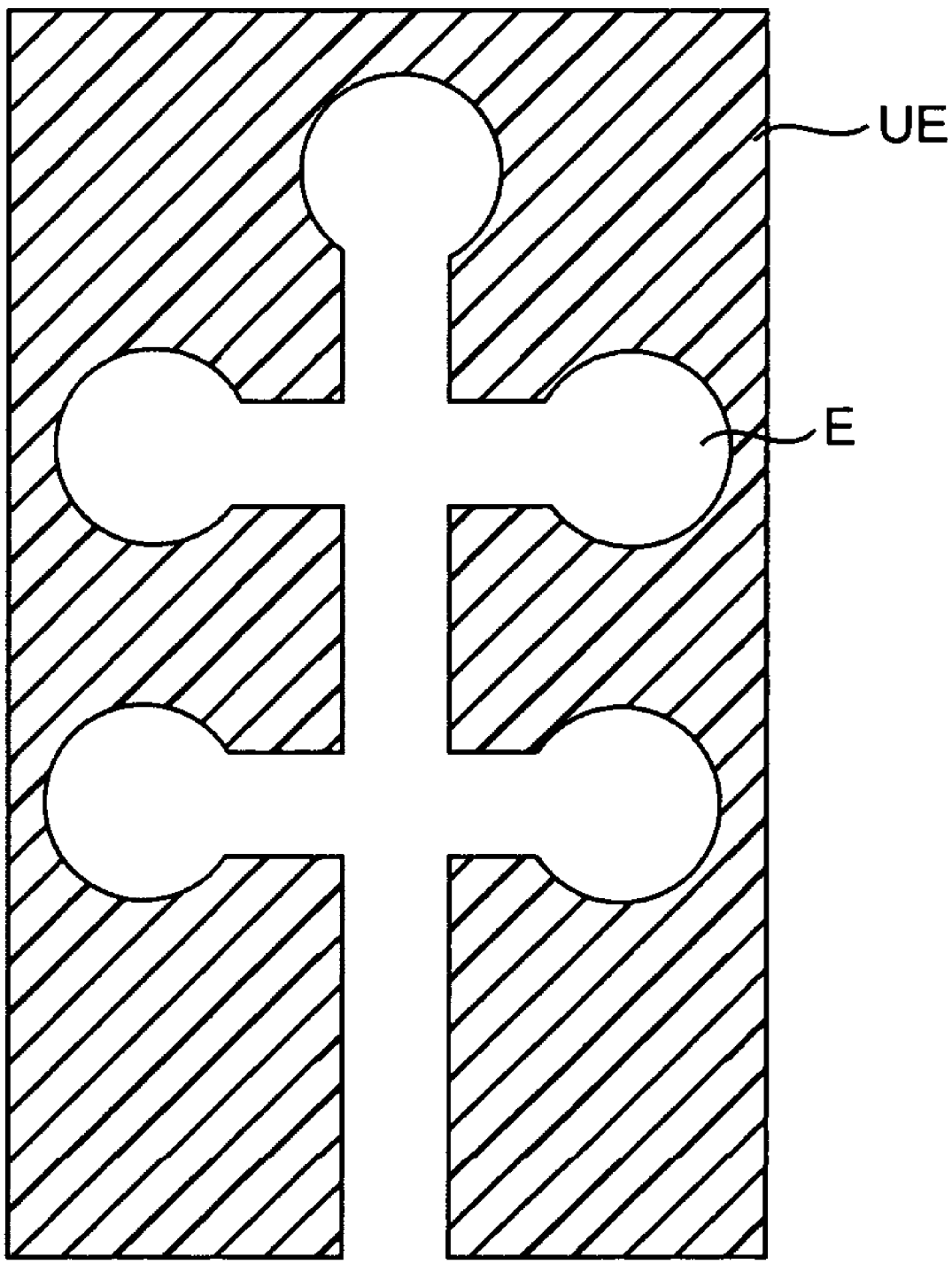

An exemplary configuration of a mask or reticle used with negative photoresist is shown in FIG. 2C. Here, the polymers in the resist become cross-linked in the areas that are exposed (E) to UV light. These cross-linked polymers are insoluble in the solvent selected to dissolve the resist from the unexposed (UE) regions of the membrane during development. An exemplary configuration of a mask or reticle used with positive photoresist is shown in FIG. 2D. Here, the region exposed (E) to UV light converts to a soluble form (e.g., a carboxylic acid), which may be dissolved away using a suitable solvent (e.g., a weak water-based alkali solvent). The unexposed (UE) region remains insoluble.

Sample distribution layers made using photoresist techniques may offer several advantages. For example, the membrane would not have to be cut or stamped out to form a pattern, thus eliminating the need for difficult and precise manufacturing procedures. Instead, manufacturing would be simple, and the process could be easily scaled using different sized and shaped photolithography masks or reticles. Similarly, crosstalk between different test sites would be eliminated.

As noted above, the cartridges may comprise any number of test sites and test site read zones and have any number of configurations. For example, the cartridge may have two or more, three or more, four or more, five or more, six or more, eight or more, or ten or more test sites and corresponding read zones, and the like. Indeed, any number of test sites may be used as practicable or desirable. Some of these test sites may be used for redundancy or for control testing purposes.

Figure 3:
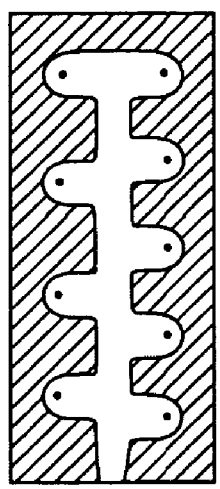
FIGS. 3A-3G depict exemplary sample distribution layer configurations.
Figure 3:
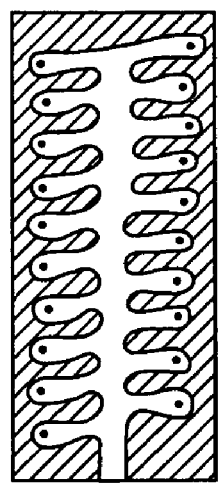
Figure 3:
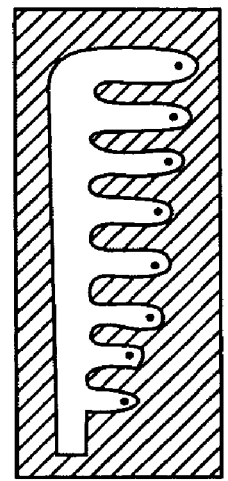
Figure 3:
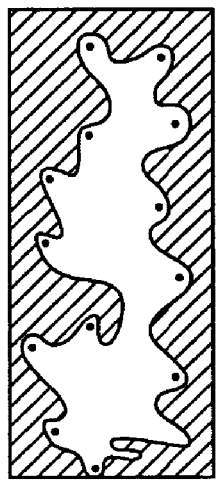
Figure 3:
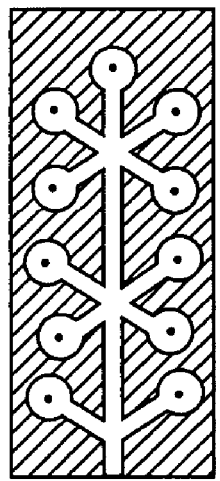
Figure 3:
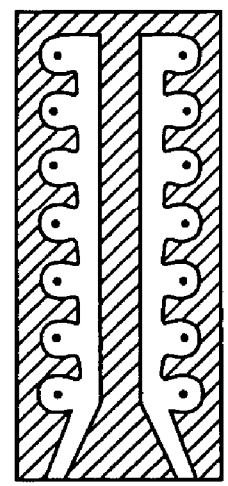

Shown in FIGS. 3A-3G are illustrative configurations of sample distribution layers suitable for use with the cartridges herein described. The sample distribution layer may provide for multiple test site locations (as illustrated by the black dots) in an orderly fashion as depicted in FIG. 3A. The sample distribution layer may also provide for multiple test sites throughout the cartridge in order to optimize the space available for the test sites as demonstrated in FIG. 3B. The sample distribution layer may be configured such that all the test sites are on one side of the cartridge as in FIG. 3C.

Figure 3G:
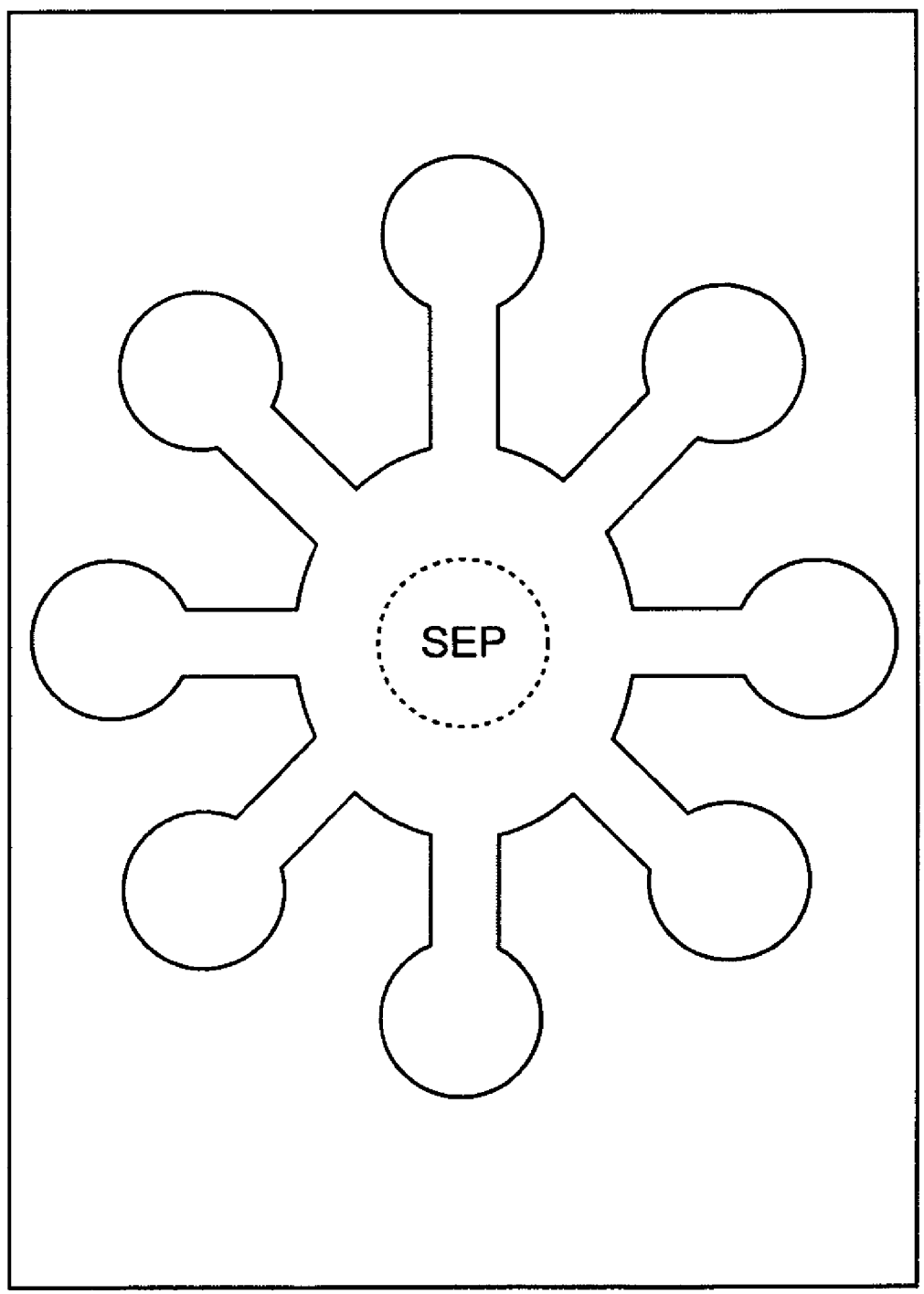

The sample distribution layer may also be amorphous in order to provide for a random distribution of the test sites, as depicted in FIG. 3D. Another variation of the sample distribution layer, configured to provide a star type of configuration is shown in FIG. 3E. It should be pointed out that the sample distribution layer may have more than one sample entrance port, as shown in FIG. 3F. In this way, two different samples may be tested simultaneously if desirable (for example, two samples of blood, a sample of urine and blood, and the like). It should be understood, that while two different sample entrance ports are depicted in FIG. 3F, any number of ports (e.g., 3, 4, 5, or more) may be used. FIG. 3G depicts one variation where the test sites and read zones are radially distributed around a sample entrance port (SEP). In this way, equal sample distribution to the test sites may be facilitated. Again, because the location of the read zones is identified by the system or device prior to testing, the sites may be located anywhere throughout the cartridge.

Figure 4:
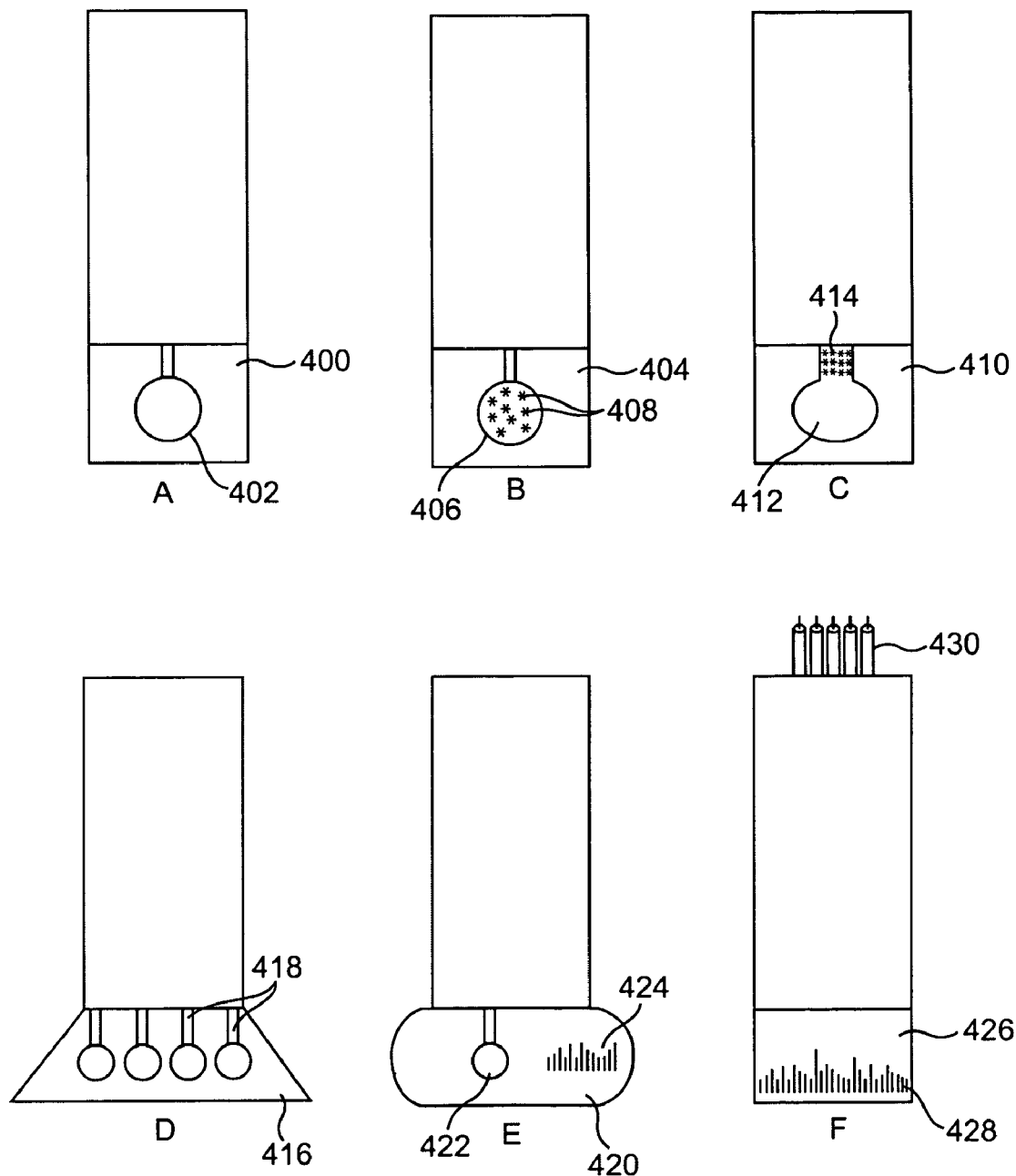
FIG. 4A illustrates a sample distribution layer having a portion configured to protrude from the port of a corresponding device, where the portion comprises a sample collection port.
FIG. 4B illustrates a sample distribution layer having a portion configured to protrude from the port of a corresponding device, where the portion comprises a sample collection port having a red blood cell separator homogenously mixed therethroughout.
FIG. 4C illustrates a sample distribution layer having a portion configured to protrude from the port of a corresponding device, where the portion comprises a sample collection port, where the entrance to the sample distribution layer has a red blood cell separator barrier.
FIG. 4D illustrates a sample distribution layer having a portion configured to protrude from the port of a corresponding device, where the portion has multiple sample collection ports.
FIG. 4E depicts a sample distribution layer having a portion configured to protrude from the port of a corresponding device, where the portion has both a sample collection port, and a unique identifier tag.
FIG. 4F depicts a sample distribution layer having electrochemistry capabilities and a portion configured to protrude from the port of a corresponding device, where the portion has a unique identifier tag.

The cartridges may also be designed such that a portion of the cartridge is configured to protrude from the port of a corresponding device. This may, for example, help with the insertion and removal of the cartridge in the device, in the case that the device does not have an automatic insertion and ejection feature. Top views of illustrative depictions of such cartridges are shown in FIGS. 4A-4F. In FIG. 4A, the protruding portion (400) has a sample collection port (402) thereon. In this way, the cartridge may first be inserted into the device, and then the sample placed in the sample collection port (402), which protrudes from the device port.

A similar configuration is shown in FIG. 4B. Shown there is protruding portion (404) and sample collection port (406).

Within sample collection port (406) is a red blood cell separator (408). Red blood cell separators are well known in the art, and can comprise for example, certain plant proteins (e.g., lectins, soybean hemagglutinins, etc.), certain anti-red blood cell antibodies (e.g., α-RBC), or certain polymeric materials, as described below. Shown in FIG. 4C is a protruding portion (410) having a sample collection port (412) thereon. A red blood cell separator barrier (414) lines the entrance to the sample distribution layer in order to separate out the red blood cells prior to testing.

FIG. 4D shows another configuration of the cartridge having a protruding portion (416). As demonstrated by FIG. 4D, the protruding portion may have any type of configuration or geometry. For example, it may be narrower than the remaining cartridge, or may be wider than the remaining cartridge as shown in FIG. 4D. In addition, the protruding portion may have multiple sample collection ports (418) thereon. As described above, these collection ports may further comprise a red blood cell separator.

FIG. 4E provides an illustration of a cartridge having a protruding portion (420). In this variation, the protruding portion has the shape of an elongated oval, but as described above the protruding portions may have any desirable geometry. The protruding portion of FIG. 4E has a sample collection port (422) and a unique identifier tag (424). The unique identifier tag (424) is shown as a bar code, but any unique pattern may be used. The pattern may be produced for example, by mechanical methods, or by printing. Similarly, the unique identifier tag may be a microchip or the like. As described above, the unique identifier tag can enable the system or device to determine the location, number, and types of test sites and read zones on the cartridge prior to testing, or can directly or indirectly provide calibration, algorithm, and test procedure information. As noted above, in the case where the unique identifier tag is outside the port, the device may comprise a scanning window to image the tag (similar to those used at grocery stores), a scanning or swiping slot (similar to those used for credit cards), and the like. In this way, the tag can be read by the device prior to its insertion. However, the cartridge may also be fully inserted into the device so that the unique identifier tag may be read, and then ejected so that the protruding portion is again outside the device port.

Also shown in FIG. 4F are connectors (430) to enable electrochemical analysis. For example, connectors (430) may plug into a corresponding socket within the device. Similarly, the connectors may instead be POGO pins, for attachment to a corresponding socket. It should be understood that while FIGS. 4A-4F depict various configurations in which the cartridge has a portion configured to protrude from a corresponding device, the cartridges need not have such a protruding portion, such as those cartridges described above.

Figure 5A:
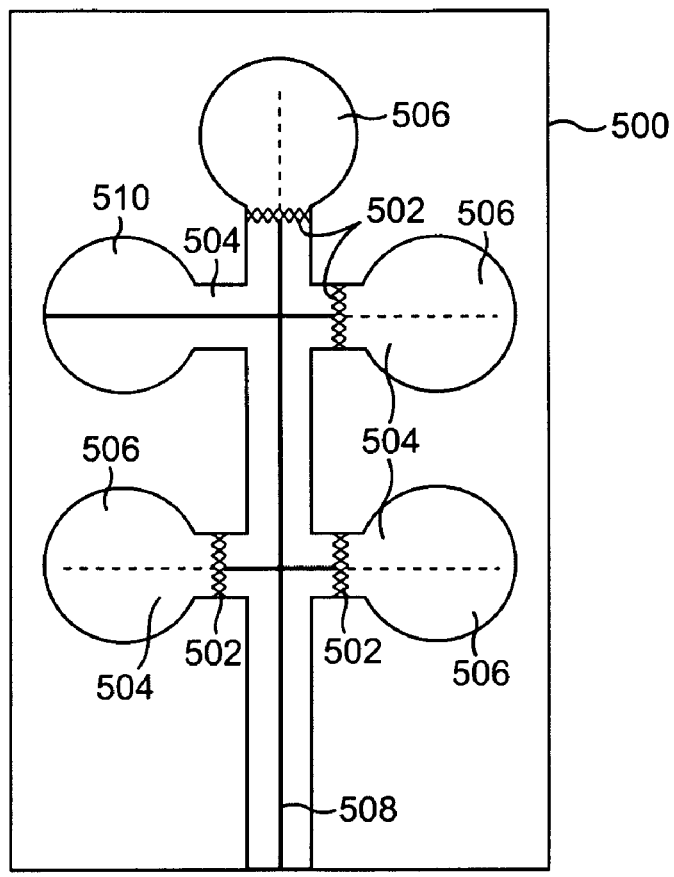
FIG. 5A illustrates a sample distribution layer where one test site receives whole blood for testing, while the others receive plasma.

FIG. 5A shows a configuration that uses red blood cell separators in the sample distribution layer itself. In this way, only those tests that require red blood cell removal will have a red blood cell separator. One way to accomplish this is shown in FIG. 5A. Shown there is sample distribution layer (500) configured for the detection of five analytes. Red blood cell separator barriers (502) may be placed immediately prior to the test site openings (504). Thus, as whole blood (508) flows through the sample distribution layer and encounters the red blood cell separator barriers (502), red blood cells are removed from the sample leaving only plasma (506). Plasma (506) continues through test site opening (504) for testing. Similarly, where no red blood cell separator barrier (502) is present, whole blood continues through the test site opening (504) for testing, as depicted by (510). While the red blood cell separators (502) are depicted in FIG. 5A as being of the same general nature, it should be understood that each red blood cell separator may be different if desirable. That is, one red blood cell separator may use plant proteins, while another may use anti-red blood cell antibodies.

The red blood cell separators may also be incorporated into a polymer bead. The bead could swell, for example, when contacted by a sample of whole blood. However, the pores in the swelled polymer bead could be configured to be small enough to exclude red blood cells, allowing only plasma to pass through. Examples of suitable polymers for forming such beads are acidic or basic hydrogels, which are triggered to swell by a change in pH, and ionic hydrogels, which are triggered to swell by a change in ionic strength. These are known in the field of controlled drug delivery. Hydrogels made with polyvinyl alcohol are described in, e.g., U.S. Pat. No. 6,608,117, which is hereby incorporated by reference in its entirety. Other suitable hydrogel materials include hydrolyzed polyacrylonitrile, polyacrylamide, starches, gelatins, and the like.

Figure 5B:
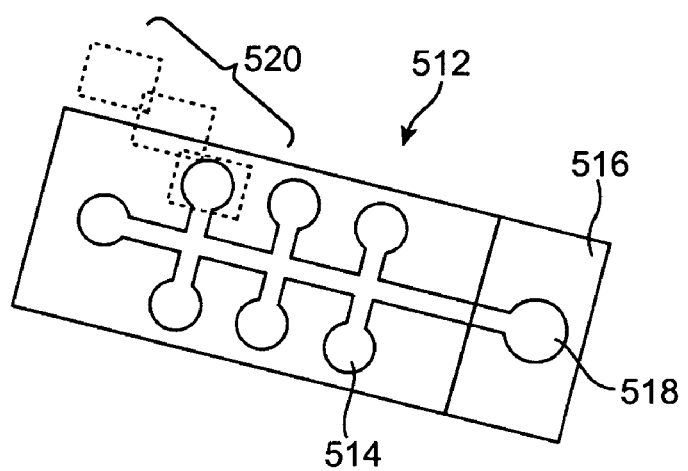
FIG. 5B shows a sample distribution layer having a portion configured to protrude from the port of a corresponding device, and a layered test site.

FIG. 5B shows how the test site may be located on top of a sample distribution layer. Shown there is cartridge (512) comprising a sample distribution layer (514), and a portion configured to protrude from a corresponding measurement device (516). In this example, the portion (516) has a sample port (518) thereon. Also shown is test site (520), here shown as three layers. As explained above, any number of layers may be used for the test sites.

Figure 6A:
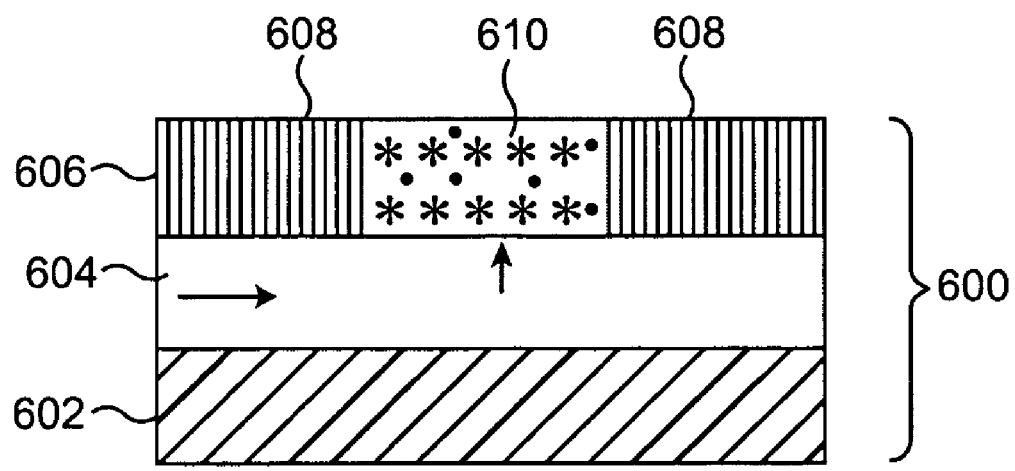
FIGS. 6A and 6B depict cross-sectional views of illustrative cartridge configurations.
Figure 6B:
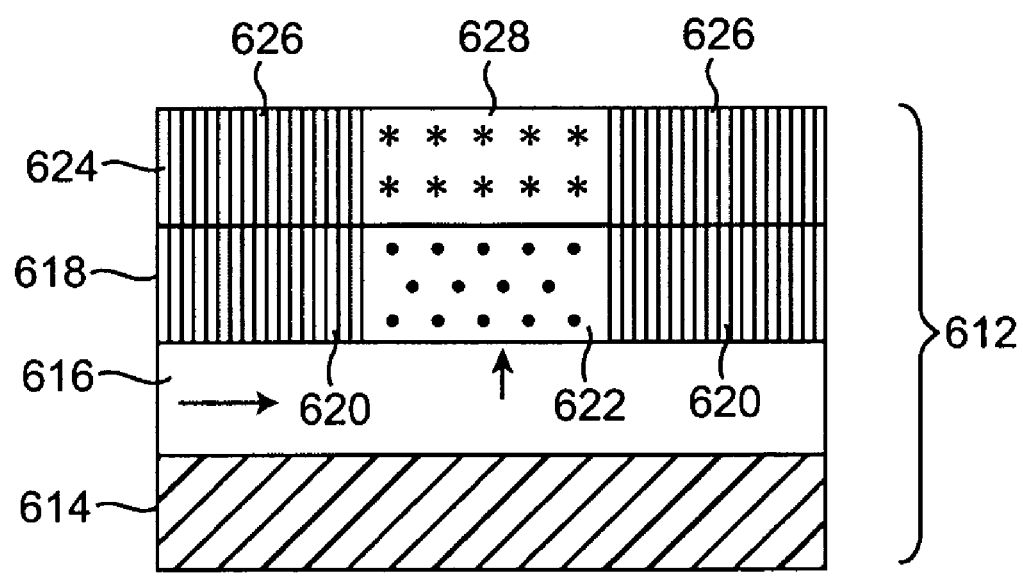

As noted above, any number of detection or quantification techniques may be used with the cartridges and devices described herein. That is, one technique may be used at one test site, while another technique may be used at several others. Suitable techniques include enzyme assays, immunoassays, fluorescence labeling and measurement, chemiluminescent labeling and measurement, electrochemiluminescent labeling and measurement, reflectance measurement, transmittance measurement, absorbance measurement, turbidity measurement, electrochemistry, and the like. FIGS. 6A and 6B provide illustrative depictions of sample test site configurations.

Shown in FIG. 6A is a cross-section of a cartridge (600) suitable for use with the devices described herein. The cartridge (600) comprises a bottom layer (602), a sample distribution layer (604), and a test site layer (606). The test site layer (606) depicted in FIG. 6A has two non-porous portions (608) to prohibit fluid from flowing therein. The test site layer also has a conjugate zone (610). As used herein, the term conjugate zone is meant to describe an area of the test site occupied by a diffusely immobilized conjugate, a conjugate being any label coupled to a specific binding member of a binding pair. Exemplary binding members include, without limitation, analytes, analyte analogs, antibodies, nucleic acids or fragments thereof, lectins, and the like. Exemplary labels include, without limitation, fluorescent molecules or microparticles, colored molecules or microparticles, enzymes, coenzymes, and the like. Shown in conjugate zone (610) are diffusely immobilized conjugates, which will bind to an analyte of interest or to a non-diffusely immobilized specific binding member.

In the variation depicted in FIG. 6A, for example, the specific binding member may be an antibody, and the test site may be configured to run a homogenous immunoassay (i.e., an immunoassay that does not require the separation of free conjugate from bound conjugate prior to measurement). Also typically included in the conjugate zone are other reagents, substrates, enzymes, and indicators, as needed to run a given reaction. Thus, in this design, the conjugate zone and indicator zone (i.e., the area of the test site occupied by signal-developing reagents such as enzymes and enzyme substrates) are the same. These zones will be described in more detail below when reference is had to various test site configurations.

Figure 6C:
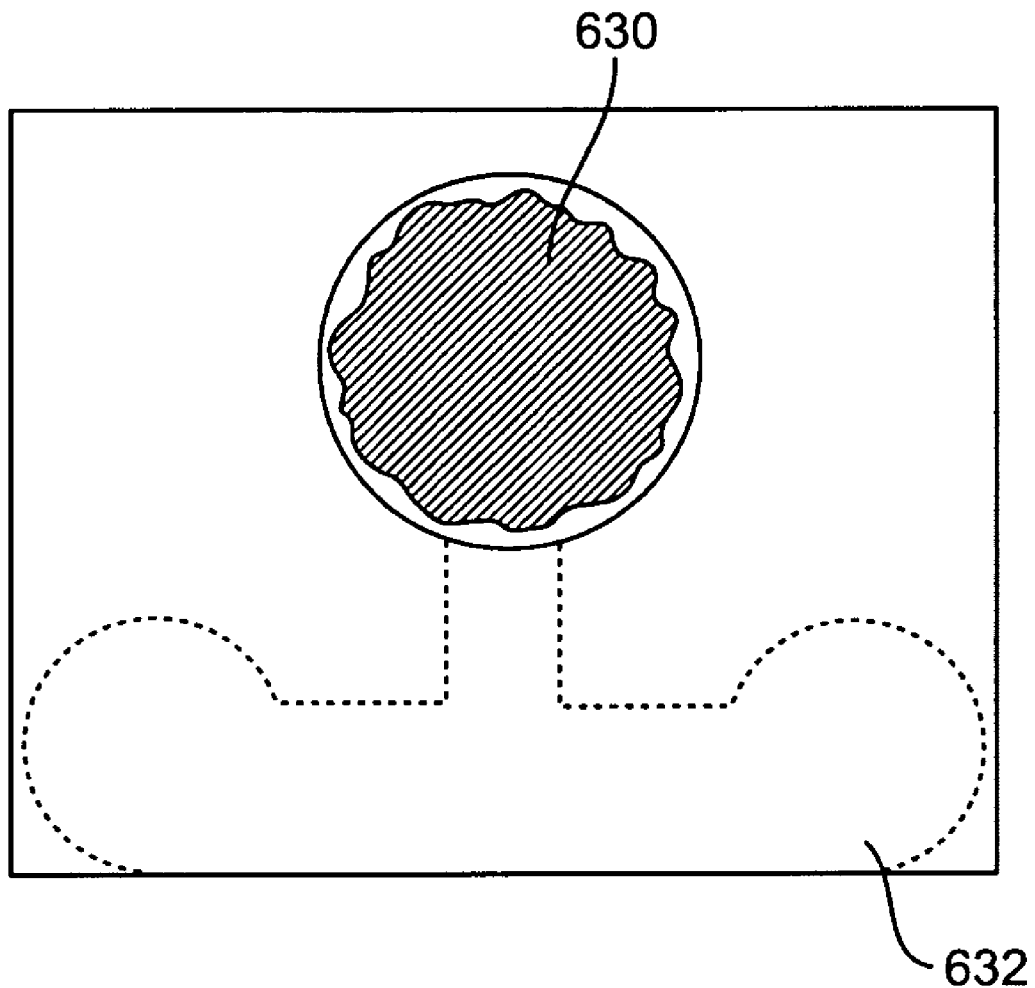
FIG. 6C provides a top view of FIGS. 6A and 6B.

Another variation is depicted in FIG. 6B, this time having two test site layers. Shown there is a cross-section of a cartridge (612). The cartridge comprises bottom layer (614), sample distribution layer (616), and test site layers (618) and (624). Test site layer (618) has non-porous portions (620) and a conjugate zone (622). Test site layer (624) has non-porous portions (626) and an indicator zone (628). As with the test site depicted in FIG. 6A, the test site in FIG. 6B may be configured to run a homogenous immunoassay. Here however, the conjugate zone and indicator zones are separated. In this way, the indicator may be separate from the specific binding member, which may be advantageous for example, to reduce the generation of background color. FIG. 6C provides a top view of the test sites of FIGS. 6A and 6B. As shown there, the analyte will be detected immediately above the conjugate zone location (630). The sample distribution layer within the cartridge is depicted with dashed lines as (632).

Figure 7A:
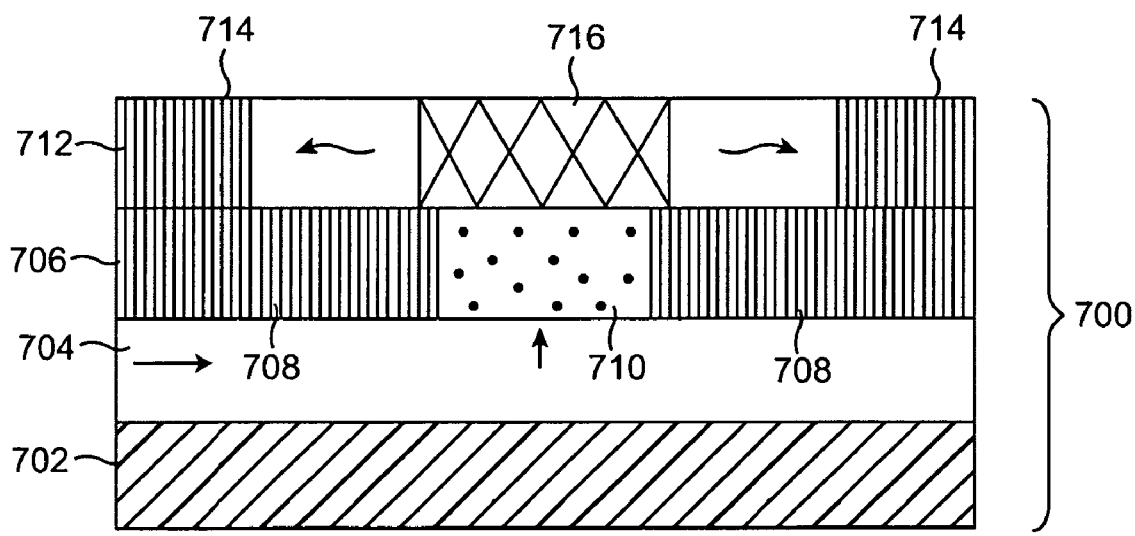
FIG. 7A depicts an illustrative cross-sectional view of a configuration suitable for use with the cartridges herein described.

FIG. 7A provides a cross-section of another suitable cartridge configuration, here having a test site with separate conjugate and capture zones. Thus, for example, the test site of FIG. 7A may be configured to perform a heterogeneous immunoassay (i.e., an immunoassay requiring the separation of free conjugate from bound conjugate prior to measurement). Cartridge (700) comprises bottom layer (702), sample distribution layer (704), and test site layers (706) and (712). Test site layer (706) has non-porous portions (708), and a conjugate zone (710). The conjugate zone (710), similar to that described above, may contain conjugates and/or other reagents (here shown by dots). Immediately above the conjugate zone (710) is a capture zone (716) within test site layer (712) where the conjugate is captured via binding or reaction. As used herein, the phrase "capture zone" is meant to describe an area of a test site wherein a conjugate is bound by a non-diffusely immobilized specific binding member. Additional fluid, containing non-bound reagents, continues to flow through test site layer (712) until it reaches non-porous barriers (714).

Figure 7B:
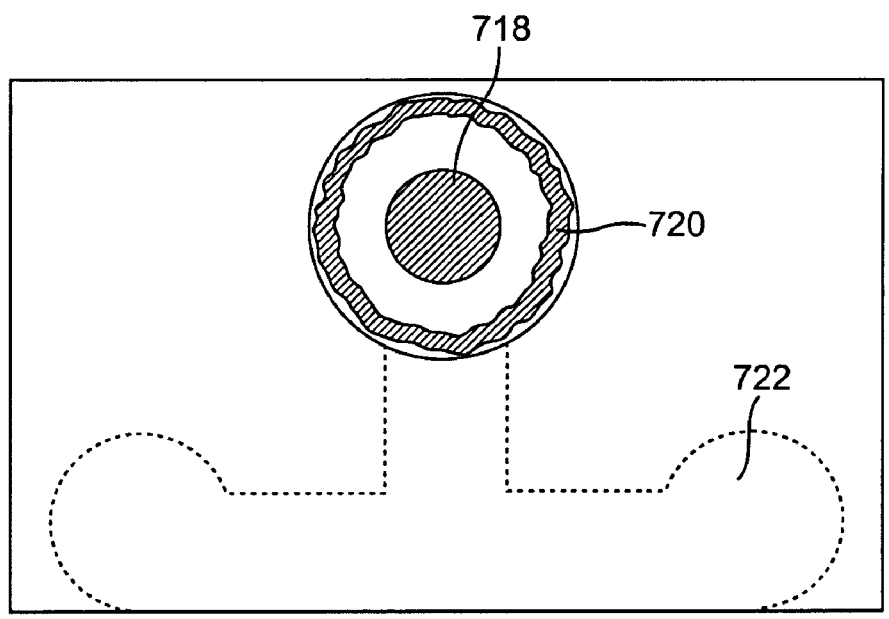
FIG. 7B is a top view of FIG. 7A.

A top view of FIG. 7A is provided in 7B. As can be seen, the conjugate is captured for detection at location (718) corresponding to capture zone (716). Non-captured reagents and additional reagent material are washed out to location (720), which corresponds to locations before non-porous regions (714). Also shown in FIG. 7B is sample distribution layer (722), here shown as dashed lines because it is located two layers below the top most test site layer.

Figure 8A:
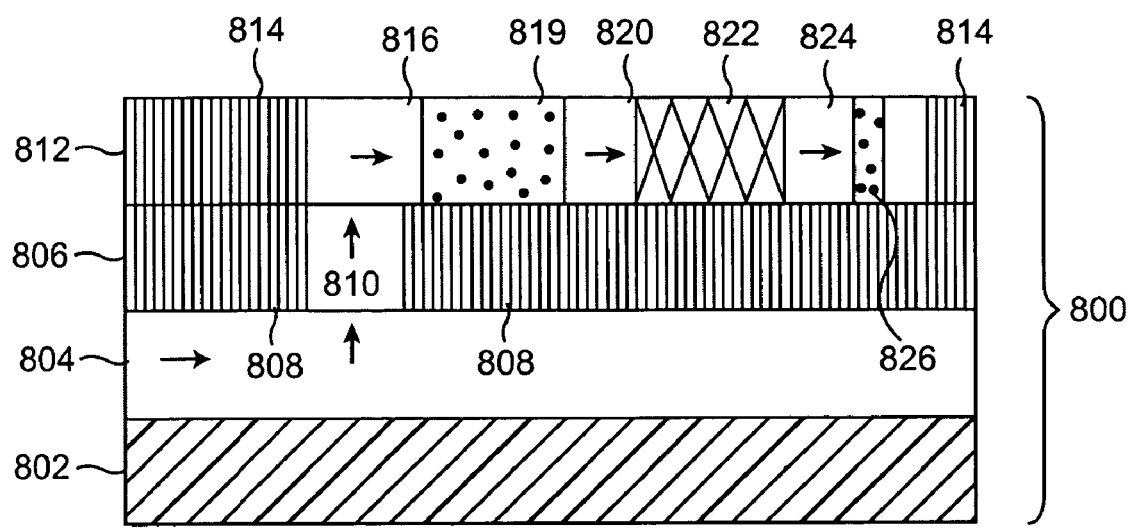
FIG. 8A depicts an illustrative cross-sectional view of a configuration suitable for use with the cartridges herein described.
Figure 8B:
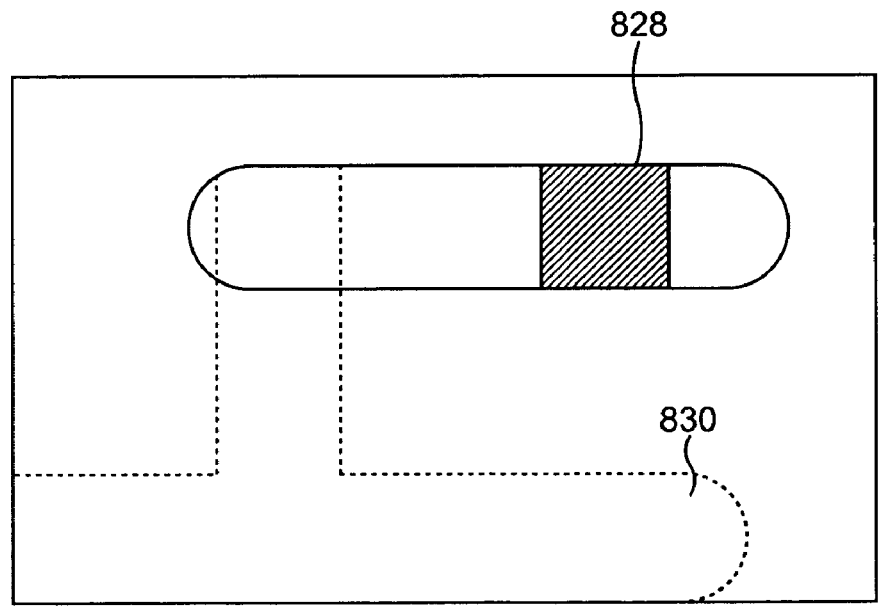
FIG. 8B is a top view of FIG. 8A.

FIG. 8A provides another cross-sectional depiction of a suitable cartridge configuration. Similar to the configuration of FIG. 7A, the test site may be configured to perform a heterogeneous immunoassay (e.g., sandwich, competitive, subtractive, etc.), except that in this configuration, the conjugate zone (818) and the capture zone (822) are in the same test site layer (812). Here, cartridge (800) comprises bottom layer (802), sample distribution layer (804), and test site layers (806) and (812). Test site layer (806) has non-porous portions (808) and a porous portion (810) for fluid to flow therethrough. In this way, the sample can flow from sample distribution layer (804) through porous portion (810) and to test site layer (812) to porous portion (816). The sample then flows through conjugate zone (818) where the analyte binds or reacts with the reagents contained therein. The reacted analyte (for example, a complex between the analyte and its labeled specific binding member, or labeled conjugate) then continues to flow through porous portion (820), and to capture zone (822) where the free conjugate or the analyte:: conjugate complex is captured via reaction or binding. Additional un-reacted analyte and unbound reagent continue to flow through porous portion (824), but stop at a place (826) before non-porous portion (814). A top view of FIG. 8A is provided in FIG. 8B. The read zone for detection is shown at location (828), which corresponds to capture zone (822). The sample distribution layer is shown as (830).

Figure 9A:
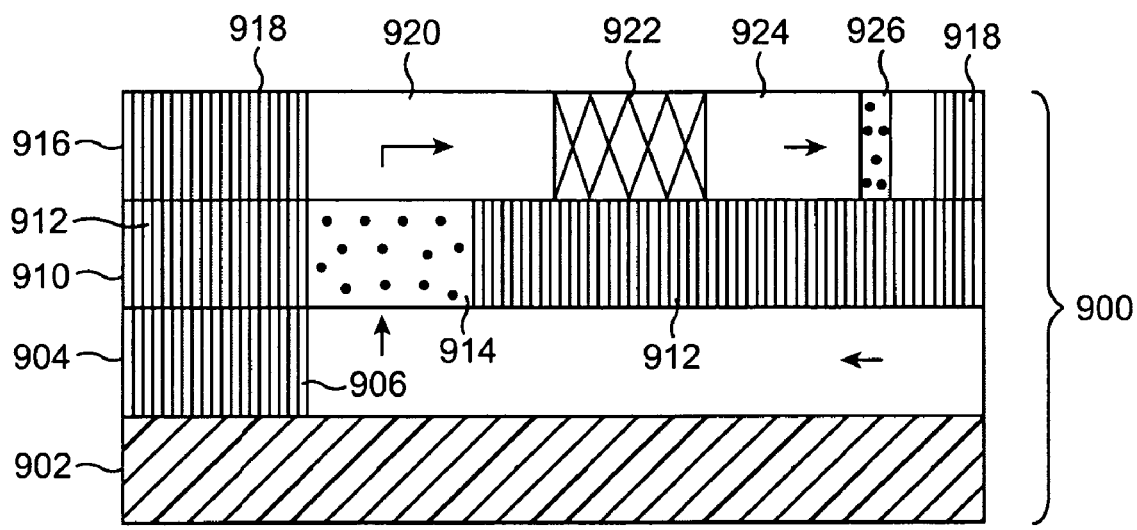
FIG. 9A depicts an illustrative cross-sectional view of a configuration suitable for use with the cartridges herein described.
Figure 9B:
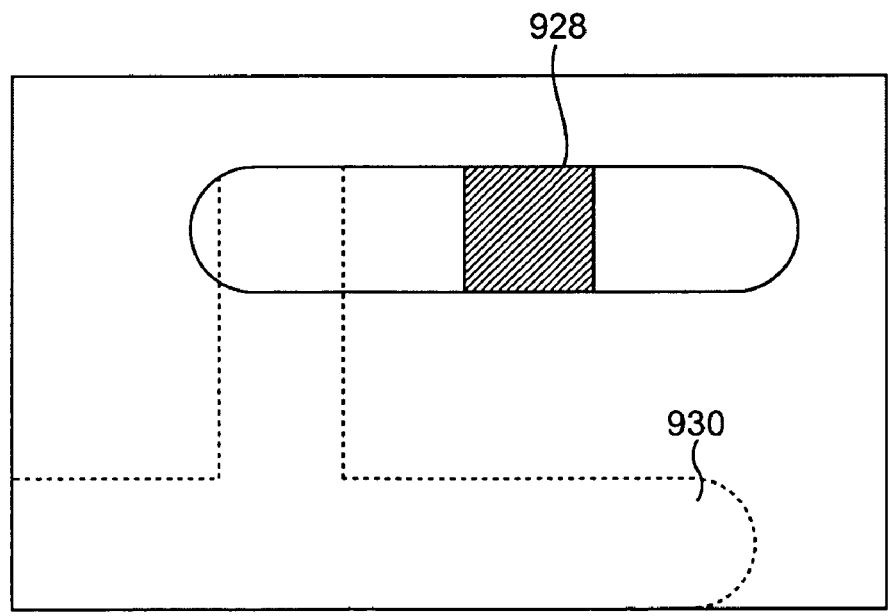
FIG. 9B is a top view of FIG. 9A.

Another configuration of a suitable cartridge is depicted in FIG. 9A. Similar to the cartridge depicted in FIG. 8A, the test site of the cartridge of FIG. 9A may be configured to run a heterogeneous immunoassay. Here the conjugate zone (914) is not in the same test site layer (916) as the capture zone (922). Instead, the conjugate zone (914) is in test site layer (910). The conjugate zone (914) is surrounded by non-porous regions (912). In this configuration, the sample flows through sample distribution layer (904), as indicated by the arrows, through the conjugate zone, and then through to test site layer (916). The free conjugate or analyte conjugate complex is then captured at capture zone (922). Unreacted analyte and unbound reagent continue to flow through porous portion (924) until they stop at a location (926) before non-porous region (918). A top view of FIG. 9A is provided in FIG. 9B. The read zone for detection is located at position (928), which corresponds to capture zone (922). The sample distribution layer is shown as (930).

The capture zone may be produced by depositing reagent microparticles with the desired component (e.g., an antibody or antigen) onto a membrane or other porous material. The reagent microparticles may be adsorbed or chemically coupled to the surface of the membrane or porous material. In addition, the size and chemical properties of the microparticles can be arranged so that they are unable to migrate (e.g., the diameter of the microparticles may be configured to be larger than the average pore size of the capture zone material). The capture zone may also be produced by direct binding of the desired component (antibody, antigen, antigen-analog, etc.) to the membrane or porous material by procedures familiar to those skilled in the art.

As noted above, the systems, devices, and cartridges described here are configured to allow testing of more than one analyte, using more than one measurement technique. That is, a cartridge may have 5 test sites for example, one of which is configured to employ fluorescence measurement, three of which are configured to employ reflectance measurements, and one of which is configured to employ chemiluminescence measurement. While test sites capable of performing electrochemical detection have not been shown in detail throughout the figures, it should be understood that cartridges having test sites capable of performing electrochemical detection are within the scope of the invention (e.g., cartridges with various electrochemical sensors or cartridges with test sites that have electrodes in contact with electrochemical reagents). Test site configurations are also provided that allow for optical transmission measurements.

Figure 10:
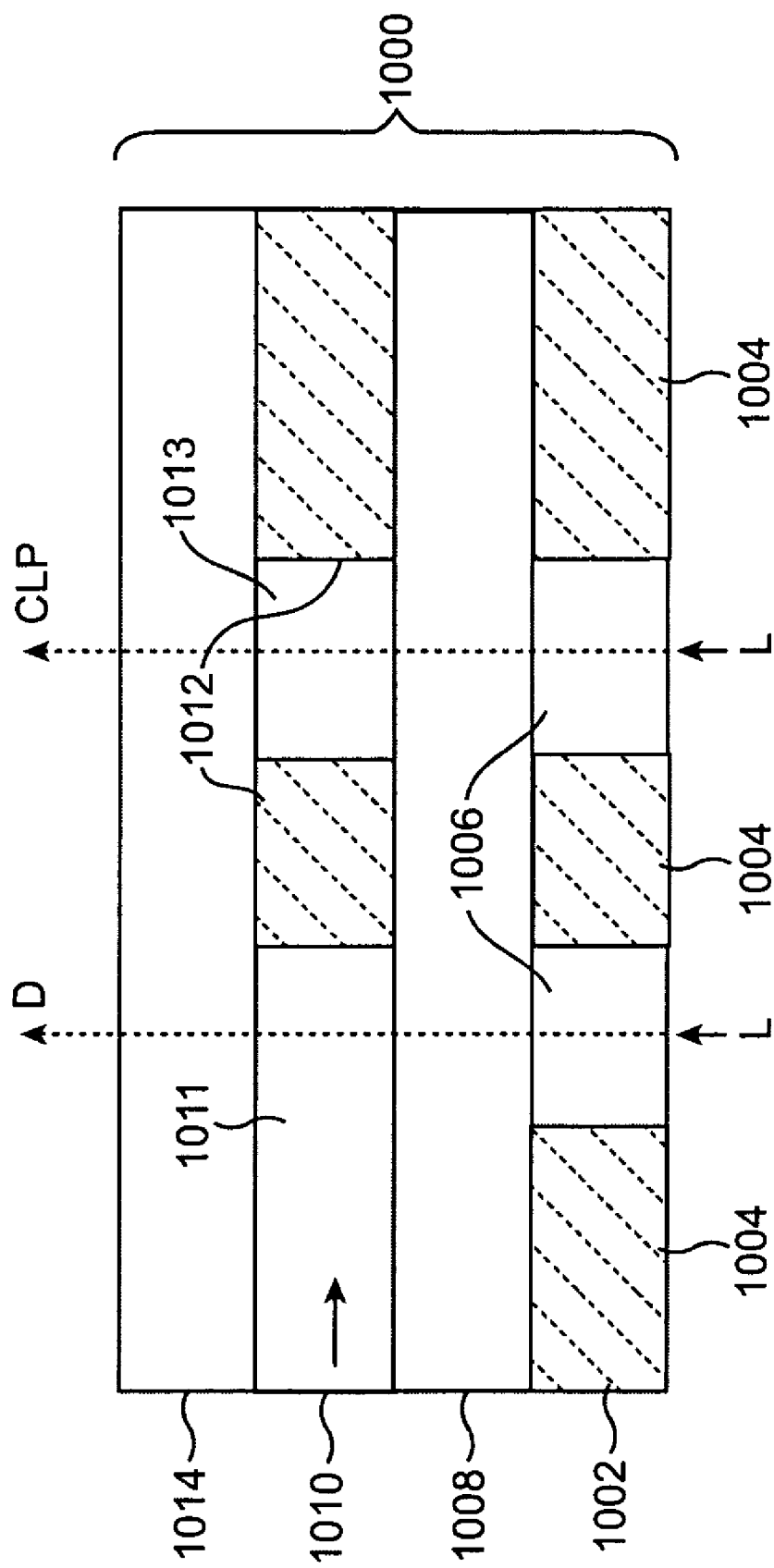
FIG. 10 depicts an illustrative cross-sectional view of a configuration suitable for use with the cartridges herein described when optical detection is required.

Depicted in FIG. 10, is a cross-section of a suitable cartridge configuration illustrating a test site allowing for optical measurements. As shown, cartridge (1000) comprises nonporous bottom layer (1002), nonporous transparent membrane layer (1008), sample distribution layer (1010), and nonporous transparent top layer (1014). The bottom layer (1002), and sample distribution layer (1010) have several non-transparent regions depicted as (1004), and (1012) respectively. In this instance, non-transparent regions (1012) are also non-porous in order to prohibit the sample flow therethrough. In this way, light (L) may be illuminated through transparent portions (1006) of bottom layer. Sample flows from the left into sample distribution layer (1010).

In this configuration, light (L) passes through sample distribution layer (1010) where it will shine through the sample and analytes contained therein. However, because the sample is prevented from passing through non-porous region (1012), the transparent region (1013) will contain no sample, and hence no analyte, and may thus be used as a control. The light (L) that shines through test region (1011) can detect an analyte at its corresponding wavelength, and will pass the information on to detector (D). Similarly, the light (L) shining through the control region (1013) will serve as the control light path (CLP).

Figure 11A:
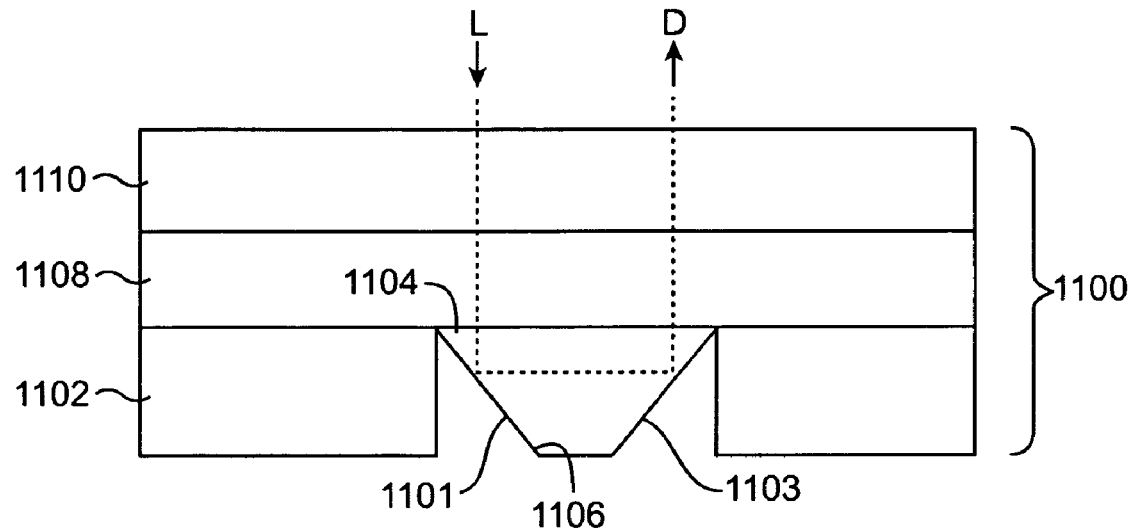
FIGS. 11A and 11B depict illustrative cross-sectional views of configurations suitable for use with the cartridges described here, when optical detection is required.
Figure 11B:
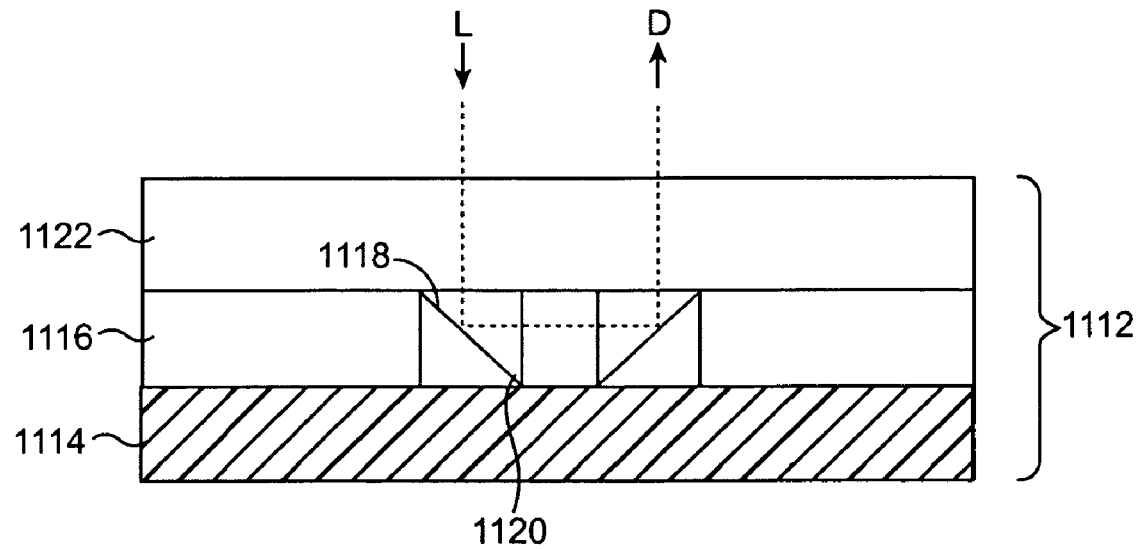

FIGS. 11A and 11B show variations of cartridge configurations employing various transparent regions. As shown in FIG. 11A, cartridge (1100) comprises nonporous bottom layer (1102), sample distribution layer (1108), and nonporous top transparent layer (1110). In this variation, light (L) from a suitable light source is illuminated through the top transparent layer (1110), through the sample distribution layer (1108), and then reflected off a portion (1101) of the bottom layer (1102). The reflected light then reflects off opposite portion (1103) of bottom layer (1102) and continues to travel back up through sample distribution layer (1108) and top transparent layer (1110) to be detected by detector (D). The portion of the bottom layer for reflecting the light may be made in any suitable manner. For example, the bottom layer may be molded to include the various angles, or additional portions may be adhered to the bottom layer in order to create the angles as necessary. The angles (1104) and (1106) may be adjusted as desired to increase, decrease, or change the pattern of the reflected light.

The configuration of FIG. 11B is similar to the configuration of FIG. 11A, except that the portion configured to reflect light is in the sample distribution layer (1116) as opposed to bottom layer (1114). Accordingly, since the portion configured to reflect the light is not in the bottom layer (1114), the bottom layer need not be transparent. Having the portion configured to reflect the light be located in the sample distribution layer (1116) may help increase detection sensitivity. As in the case with the configuration of FIG. 11A, the angles (1118) and (1120) in FIG. 11B, may be adjusted in any suitable fashion to adjust the length and pattern of the light reflected through the portion.

IV. Conjugate or Indicator Zone Configurations

As described above, there are a number of suitable conjugate or indicator zone configurations. The configuration selected is typically dependent on the chemical nature of the test to be performed. Generally speaking, these configurations can be designed by giving consideration to the concentration range of the analyte to be measured, and the molecular weight and structure of the analyte.

For example, some analytes may be present in high concentrations and will be detectable as a result of a reaction with enzymes or color-forming reagents. These analytes can be measured directly, or upon complex formation or reaction with a reagent in an indicator zone. Exemplary analytes falling within this category include lithium, sodium, hemoglobin, bilirubin, and the like.

The analyte may also be non-enzymatically, or enzymatically redox reactive. These types of redox reactions may occur with or without the consequent production of a common redox intermediate such as nicotinamide adenine dinucleotide in an oxidized or reduced form ("NAD" or "NADH"), nicotinamide adenine dinucleotide phosphate ("NADP"), flavine adenine dinucleotide in an oxidized or reduced form ("FAD" and "FADH$_2$"), and hydrogen peroxide. Similarly, these reactions may occur with or without the gain or loss of electrons from an electrochemical sensor. When redox intermediates are produced, they may optionally oxidize or reduce a chromogenic substrate. Analytes suitable for detection in this fashion include, without limitation, total cholesterol, HDL-cholesterol, glucose, β-hydroxybutyrate, hemoglobin, and the like.

Some analytes can be cleaved by a hydrolytic enzyme in order to produce a substance that either has properties allowing it to be detected directly by physical methods (e.g., colorimetry, reflectometry, fluorescence, electrochemistry, etc.) or that has redox reactivity similar to the cases described above (e.g., cholesterol esters, triglycerides, etc.). For analytes that are reactive by the above criteria, but are present in such low concentrations that direct redox reaction or detection will not be measurable, immunochemical or other specific binding assays may be appropriate. Similarly, for analytes that are not reactive by the above criteria, immunochemical or other specific binding assays may be appropriate.

For low molecular weight analytes having one, or a few, epitope(s) that bind an antibody, a homogeneous or heterogeneous competitive or competitive inhibition immunoassay may be appropriate. Exemplary analytes falling within this category include valproic acid, carbamazepine, cortisol, thyroxine ("T4"), triiodothyronine ("T3"), digoxin, phenytoin, phenobarbitol, theophylline, and the like.

For high molecular weight compounds with more than one epitope, a heterogeneous or homogeneous immunoassay employing one or two antibodies (sandwich, competitive or competitive inhibition) may be appropriate, depending on the analyte concentration. Analytes falling within this category include, without limitation, hemoglobin A1c ("HbA1c"), chorionic gonadotropin ("hCG"), thyroid stimulating hormone ("TSH"), high sensitivity TSH, brain natriuretic peptide ("BNP"), cardiac troponin I ("cTnI"), creatine kinase isoenzyme MB ("CKMB"), cytokines, microalbumin, myoglobin, and the like. If the analyte is present at extremely low concentrations, a sandwich immunoassay employing fluorescent microparticles or an enzyme label might be desirable. Chemiluminescent detection may also be employed to help improve sensitivity.

If the analyte is an enzyme or other macromolecule with catalytic activity, there may be more than one desirable test site configuration possible. For example, an activity assay may be performed employing one or more substrates, which are converted to one or more products that are either directly or indirectly detectable. Exemplary analytes within this category include, aspartate aminotransferase ("SGOT"), alanine aminotransferase ("ALT"), alkaline phosphatase ("ALK-P"), amylase, creatine kinase ("CK"), and the like. Similarly, a mass assay (sandwich, competitive, or competitive inhibition immunoassay), as outlined above for high molecular weight compounds may be used, for example, when the analyte is CKMB, or the like.

V. Test Site Configurations

The following are examples of various test site configurations that may be used with the cartridges herein described. It should be understood that these examples are not comprehensive or exhaustive of the many variations of test site configurations suitable for use with the described cartridges. These examples are non-limiting and for illustrative purposes only.

A. Apoenzyme Reactivation Immunoassay System ("ARIS") Assay

This type of homogeneous immunoassay is particularly amenable to small molecule analytes such as valproic acid, carbamazepine, or thyroxine, but it may also be used to detect larger analytes such as immunoglobulins. A conjugate is constructed in which the analyte is coupled covalently to flavin adenine dinucleotide ("FAD"). This conjugate competes with the unlabeled analyte in the sample for binding to a specific antibody. FAD-conjugated analyte that is not bound to antibody, due to competition with free analyte from the sample, is free to bind to apo-glucose oxidase, activating it. The resulting glucose oxidase activity is directly proportional to the amount of analyte in the sample.

For example, making reference now to FIG. 6A, conjugate zone (610) could contain apo-glucose oxidase, a preformed complex of FAD-analyte::anti-analyte antibody, glucose, horseradish peroxidase ("HRP"), and a chromogenic, fluorogenic, or chemiluminescent HRP substrate. When the sample competes off the FAD-analyte from the FAD-analyte::anti-analyte antibody complex, the FAD-analyte is free to bind to apo-glucose oxidase, thus activating it. In FIG. 6B, conjugate zone (622) could contain apo-glucose oxidase, a preformed complex of FAD-analyte anti-analyte antibody, and HRP, while indicator zone (628) could contain glucose and a chromogenic, fluorogenic, or chemiluminescent HRP substrate.

B. Enzyme Multiplied Immunoassay Technique ("EMIT") Assay

This type of homogeneous immunoassay is particularly amenable to small molecule analytes, such as phenytoin, valproic acid, and thyroxine, but it may also be used to detect larger analytes such as immunoglobulins. A conjugate is constructed in which the analyte is covalently coupled to an enzyme. This conjugate competes with the unlabeled analyte in the sample for binding to a specific antibody. In one example, analyte-conjugated enzyme bound to antibody exhibits reduced activity. Analyte present in the sample will compete for antibody binding, releasing the analyte-conjugated enzyme. Therefore, the higher the concentration of analyte in the sample, the higher the observed enzyme activity will be. With appropriate temperature monitoring and correction by the system or device, a reaction rate could be determined, as opposed to simply an endpoint. (Indeed, in some instances, temperature monitoring will be very desirable, for example, where the activity of an enzyme is being measured directly.)

For example, making reference now to FIG. 6A, conjugate zone (610) could contain a preformed complex of analyte-enzyme::anti-analyte antibody, along with enzyme substrates. When the sample competes off the analyte-enzyme from the analyte-enzyme::anti-analyte antibody complex, the analyte-enzyme is free to act on its chromogenic, fluorogenic, or chemiluminescent substrate. Thus, the rate of color formation is directly proportional to the concentration of analyte in the sample. Similarly, referring now to FIG. 6B, conjugate zone (622) could contain the preformed complex of analyte-enzyme::anti-analyte antibody, while indicator zone (628) could contain the chromogenic, fluorogenic, or chemiluminescent enzyme substrate.

Typical enzymes used for EMIT assays include lysozyme, glucose-6-phosphate dehydrogenase, malate dehydrogenase and β-galactosidase.

C. Competitive Binding Assay

In one version of this type of assay, the analyte in the sample competes with a labeled analyte for binding to a specific binding partner. The amount of label associated with the binding partner at the end of the assay is inversely proportional to the concentration of analyte in the sample. For example, in FIG. 7A, conjugate zone (710) might contain a preformed complex of labeled analyte: anti-analyte antibody. When the sample contacts this complex, it competes with the bound label for the antibody binding sites, displacing the label from the complex. Capture zone (716) might contain a non-diffusely immobilized antibody against the first antibody. The first antibody is captured at this site, along with its remaining bound label. The signal measured at this site is indirectly proportional to the concentration of analyte in the sample. In the case of valproate, valproate in the sample might compete with a labeled valproate analog for binding to a goat anti-valproate antibody. This antibody flows toward the capture zone, where it is captured by a donkey anti-goat antibody. Unbound analyte and labeled analyte flow radially away from the capture zone, and the signal in the capture zone is indirectly proportional to the concentration of valproate in the sample.

In another version of this assay type, the specific binding partner carries the label. In this case, the labeled binding partner that is not bound to analyte from the sample is free to bind to an analyte or an analyte analog that is, for example, immobilized in a capture zone. For example, in FIG. 8A, the conjugate zone (818) may contain one or more labeled antibodies or other binding partners, specific for the analyte to be tested. The labeled antibody or other binding partner will mix with the analyte in the sample and then flow to the capture zone (822), where that labeled antibody or binding partner not bound to the analyte can bind to analyte that has been immobilized there. For example, in the case of thyroxine, the labeled antibody may be an anti-thyroxine antibody. The labeled antibody that does not react with thyroxine in the sample will flow to the capture zone and react with a thyroxine antigen immobilized there.

D. Sandwich Binding Assay

This type of heterogeneous assay is particularly amenable to large molecule analytes with at least two specific binding sites, such as human chorionic gonadotroptin ("hCG") and thyroid stimulating hormone ("TSH"). To construct this assay, one of two specific binding partners is conjugated to a label. In the first step of the reaction, the analyte in the sample mixes with, and is bound to, the labeled binding partner. The reaction mixture then flows to the capture zone, where the labeled binding partner that has bound analyte is captured using a second binding partner for the same analyte. The signal, read at the capture zone, is directly proportional to the concentration of analyte in the sample.

For example, making reference to FIG. 8A, conjugate zone (818) could contain a diffusely immobilized labeled antibody specific for the analyte in question. When the sample contacts this antibody, the analyte binds to it. The mixture then flows on to capture zone (822), where a second antibody specific for the analyte is nondiffusely immobilized. This antibody captures the analyte::labeled antibody complex. In the case of hCG in blood, the labeled antibody in the conjugate zone may be specific for one epitope on hCG. The antibody immobilized in the capture zone would then be specific for a second epitope.

E. Sample Treatment to Develop Color

Here, a test sample can be optionally diluted and then added to the cartridge and treated with a reagent present in an indicator zone, in the diluent, in a capture zone, or all three, to produce a color reaction with a component of the sample that is detected at a read zone. In the case of hemoglobin in blood, the sample diluent can contain a detergent to lyse the red blood cells, and an oxidizing agent such as potassium ferricyanide to oxidize the hemoglobin to methemoglobin. The red-brown color read at the capture zone is directly proportional to the amount of hemoglobin in the sample.

F. Enzyme Assay

Here, enzyme activity is measured by adding a sample to a cartridge containing enzyme substrates that are diffusely immobilized in an indicator zone. The mixture flows to the indicator zone where color development (or any other detectable change) occurs. At this point, the signal is detected. The test site configuration depicted in FIG. 5 is amenable to this type of assay. For example, when testing for alanine aminotransferase ("ALT") in blood, substrates for the transaminase reaction (α-ketoglutarate and alanine, along with an appropriate buffer containing pyridoxal phosphate cofactor), pyruvate oxidase and sodium phosphate, and horseradish peroxidase and its chromogenic substrate, TMB or the like, are diffusely immobilized in the indicator zone. When the dried materials are reconstituted with a sample containing transaminase activity, color (reflectance change caused by generation of oxidized TMB chromophore) is generated at a rate proportional to the concentration of ALT.

G. Alkaline Phosphatase Assay

For alkaline phosphatase, a fluorogenic substrate such as 4-methylumbelliferone 7-phosphate (MUP) can be hydrolyzed to a fluorescent compound (methylumbelliferone) by the action of alkaline phosphatase. A solution of MUP in an appropriate buffer can be deposited onto the membrane in the indicator zone and dried. When the sample rehydrates the mixture, the MUP is hydrolyzed at a rate directly proportional to the concentration of alkaline phosphatase in the blood sample, yielding a proportionate rate of increase in fluorescence. This rate of increase in fluorescence is converted to enzyme units by the processing module according to algorithms and calibration factors stored in the memory.

H. Total Cholesterol Redox Chemical Assay

When total cholesterol is the reactive analyte, the cartridge could be configured to allow for the following chemical reactions:

| | |
|---|---|
| (cholesterol esterase) | Cholesterol Esters + $H_2O$ → Cholesterol + Fatty Acids |
| (cholesterol oxidase) | Cholesterol + $O_2$ → Cholestene-3-one + $H_2O_2$ |
| (peroxidase) (color or fluorescence) | $H_2O_2$ + Indicator → $H_2O$ + Oxidized Indicator |

I. Method of Making a Dry Reagent Test Site for Glucose

An aqueous solution of indicator (TMB, N,N,N,N-tetramethyl-benzidine—or a fluorogenic substrate such as Amplex Red® from Molecular Probes, Inc., that is oxidized to resorufin), glucose oxidase, horseradish peroxidase, and 25 mM MES buffer, pH 6, can be dispensed onto the indicator zone. The drop size will typically depend on the thickness of the support used, and may vary from about 0.1 μL to about 5 ηL. After the droplet has been absorbed by the membrane support at the indicator zone, the cartridge can then be transferred to a drying oven (40° C.) maintained at a low relative humidity (under 10%) with constant air circulation. Once the fluid has evaporated, the cartridge may be removed and transferred into a foil-laminate pouch containing a packet with a small amount of desiccant (e.g., about 0.5 g to about 1.0 g of molecular sieve material or silica gel). The pouch may then be sealed with a heat sealer and stored until the test is needed.

Again, it should be understood that in all the exemplary test site configurations described just above, the detectable change at the read zone (change in reflectance, fluorescence, color, transmittance, absorbance, etc.) need not be at a precise location on the cartridge. The array detector in combination with the processing module and its imaging analysis capability, enable the system to identify the location of the test site read zones, as well as enable the system to determine the optimal portion of the image from which to extract quantitative information.

VI. Kits

Kits for detecting or quantifying at least two different analytes are also provided. For example, the kits may comprise a system and a cartridge. The system of the kit may be any of the systems described above, for example, one comprising a device, memory, and a processing module. The device typically comprises a port configured to accept at least a portion of a cartridge, a light source, and an array detector.

In some variations, at least a portion of the cartridge is configured to protrude from the port of the device. In this way, the protruding portion may comprise a red blood cell separator, a unique identifier tag, or mixtures of both, as described above. The cartridge may also be disposable, for example, configured for a single use. The cartridge of the kits may also be packaged in a sealed, but openable, moisture resistant packaging.

Similarly, the kits may comprise the cartridge itself, or packets of various cartridges. In this way, different cartridges can be shipped together, where each cartridge has a different, or similar, diagnostic or analytical capability. The kits may also comprise instructions for using the described cartridges, devices, or systems.

VII. Methods

As should be evident from the description herein throughout, methods for detecting or quantifying at least two different analytes using the cartridges and devices herein are also provided. In general, the methods comprise the steps of acquiring calibration information for a cartridge having at least two test sites thereon, acquiring an image of the cartridge using an array device, performing an image analysis of the cartridge to identify the location of at least one of the read zones, and cycling through specific detection or quantification techniques required by the tests. At least two different detection techniques are used. In addition, methods of reviewing one or more test results, wherein the test results are produced by the methods herein described, are also provided. Methods of diagnosing or aiding diagnosis of a disease or condition using the techniques described herein are also provided.

As has been described, the systems, devices, cartridges, kits, computer readable media, and methods described herein provide for the detection or quantification of at least two different analytes in a single sample using at least two different techniques. It should be understood, however, that the systems, devices, cartridges, kits, computer readable media, and methods described, are not limited to the precise examples herein set forth. Accordingly, modifications of the above-described systems, devices, cartridges, kits, computer readable media and methods, which are apparent to those of skill in the art, are intended to be within the scope of the appended claims.

What we claim is:

1. A cartridge comprising at least one reagent and at least two test sites, each test site having at least one test site read zone for the detection or quantification of an analyte the first of the at least two test sites being comprised of more layers than the second of the at least two test sites, one of the test sites having a height greater than the other.

2. The cartridge of claim 1, wherein the testing techniques for the detection or quantification of the analytes are independently selected from the group consisting of enzyme assays, specific binding assays, immunoassays, nucleic acid hybridization assays, fluorescence labeling, chemiluminescent labeling, electrochemiluminescent labeling, fluorescence measurement, chemiluminescent measurement, electrochemiluminescent measurement, reflectance measurement, transmittance measurement, absorbance measurement, turbidity measurement, electrochemistry, and combinations thereof.

3. The cartridge of claim 1, comprising at least three test site read zones.

4. The cartridge of claim 1, comprising at least six test site read zones.

5. The cartridge of claim 1, wherein at least one test site is configured to detect or quantify an analyte that is treatment, disease, disorder, or ailment specific.

6. The cartridge of claim 1, wherein at least one test site is configured to detect or quantify an analyte that is a substance of abuse.

7. The cartridge of claim 1, wherein at least one test site is configured to detect or quantify an analyte that is a medicament or a by-product thereof.

8. The cartridge of claim 1, wherein at least one test site is configured to detect or quantify an analyte that is an environmental toxin or contaminant.

9. The cartridge of claim 1, wherein at least one test site is configured to detect or quantify an analyte that is a biological or chemical warfare agent.

10. The cartridge of claim 1, further comprising a unique identifier tag.

11. The cartridge of claim 10, wherein the unique identifier tag is selected from the group consisting of a bar code, a mechanical pattern, a microchip, and a printed pattern.

12. The cartridge of claim 1, wherein the cartridge is housed in a sealed, but openable moisture resistant package.

13. The cartridge of claim 1, configured to accept a sample volume of about 20 μL or less.

14. The cartridge of claim 1, configured to accept a sample of bodily fluid.

15. The cartridge of claim 14, wherein the bodily fluid is selected from the group consisting of whole blood, plasma, serum, sweat, saliva, tears, interstitial fluid, spinal fluid, ocular fluid, pus, milk, semen, amniotic fluid, vaginal secretions, mucous secretions, and urine.

16. The cartridge of claim 1, further comprising a bottom layer and a sample distribution layer, wherein at least a portion of said bottom layer is non-porous and the test site read zones are adjacent to or embedded within the sample distribution layer.

17. The cartridge of claim 16, further comprising a retaining layer, wherein the retaining layer is configured to adhere together the bottom layer, the sample distribution layer, and the test sites.

18. The cartridge of claim 1, wherein said cartridge comprises a portion adapted to mate with a device, said portion having at least one test site read zone.

19. The cartridge of claim 1, wherein the first of the at least two test sites has a height greater than the height of the second of the at least two test sites.

20. The cartridge of claim 16, wherein the sample distribution layer is comprised of photoresist materials.

21. The cartridge of claim 1, wherein the at least two test sites are configured to use at least two different techniques for the detection or quantification of at least two analytes, wherein the at least two analytes are structurally and chemically the same, but have different concentrations.

22. The cartridge of claim 1, wherein the number of layers in the first test site is two.

* * * * *

UNITED STATES PATENT AND TRADEMARK OFFICE
CERTIFICATE OF CORRECTION

| | | |
|---|---|---|
| PATENT NO. | : 7,887,750 B2 | Page 1 of 1 |
| APPLICATION NO. | : 10/840344 | |
| DATED | : February 15, 2011 | |
| INVENTOR(S) | : Joel M. Blatt and Carole R. Stivers | |

It is certified that error appears in the above-identified patent and that said Letters Patent is hereby corrected as shown below:

** Column 27, line 51, delete the symbol "ηL" and replace it with --μL--.

Column 28, line 58, insert a --,-- after the word --analyte--. **

Signed and Sealed this
Sixth Day of March, 2012

David J. Kappos
*Director of the United States Patent and Trademark Office*